United States Patent
Barker et al.

(10) Patent No.: US 6,981,963 B2
(45) Date of Patent: Jan. 3, 2006

(54) PRE-FILLED SAFETY DILUENT INJECTOR

(75) Inventors: John M Barker, Ventura, CA (US); Thor R. Halseth, Agoura, CA (US); Joseph Kovalski, Ventura, CA (US); Robert T. McWethy, Ventura, CA (US); Bernardo Challiol, Ventura, CA (US)

(73) Assignee: MDC Investment Holdings, Inc., Wilmington, DE (US)

( * ) Notice: Subject to any disclaimer, the term of this patent is extended or adjusted under 35 U.S.C. 154(b) by 375 days.

(21) Appl. No.: 10/099,933

(22) Filed: Mar. 13, 2002

(65) Prior Publication Data

US 2002/0177805 A1 Nov. 28, 2002

Related U.S. Application Data

(60) Provisional application No. 60/275,568, filed on Mar. 13, 2001.

(51) Int. Cl.
*A61M 5/00* (2006.01)
*A61M 5/08* (2006.01)

(52) U.S. Cl. .................... 604/90; 604/88; 604/191; 604/243

(58) Field of Classification Search ............ 604/82–90, 604/191, 198, 243, 110, 131
See application file for complete search history.

(56) References Cited

U.S. PATENT DOCUMENTS

| | | |
|---|---|---|
| 3,563,240 A | 2/1971 | Silver |
| 3,563,373 A | 2/1971 | Paulson |
| 3,570,486 A | 3/1971 | Engelsher et al. |
| 3,636,950 A | 1/1972 | Gomez et al. |
| 3,659,749 A | 5/1972 | Schwartz |
| 3,724,460 A | 4/1973 | Gomez et al. |
| 3,785,379 A | 1/1974 | Cohen |
| 3,911,916 A | 10/1975 | Stevens |
| 3,946,732 A * | 3/1976 | Hurscham ............ 604/88 |
| 4,031,892 A | 6/1977 | Hurschman |
| 4,031,895 A | 6/1977 | Porter |
| 4,055,177 A | 10/1977 | Cohen |
| 4,059,109 A | 11/1977 | Tischlinger |
| 4,122,943 A | 10/1978 | Silver et al. |
| 4,159,066 A | 6/1979 | Silver |
| 4,171,698 A | 10/1979 | Genese |
| 4,235,235 A | 11/1980 | Bekkering |

(Continued)

FOREIGN PATENT DOCUMENTS

FR 2715071 7/1995

(Continued)

*Primary Examiner*—Nicholas D. Lucchesi
*Assistant Examiner*—Roz Maiorino
(74) *Attorney, Agent, or Firm*—Stephen H. Eland; Dann, Dorfman, Herrell and Skillman

(57) ABSTRACT

A safety needle-bearing device for mixing and injecting medication from a two-chambered cartridge is provided. The device includes a needle that extends through the forward end of a barrel. A two-chambered cartridge is attached to the barrel and contains components of a medication stored separately in the chambers. A plunger in the rearward end of the cartridge can be advanced into the cartridge to combine the separate components and prepare the medication. As the cartridge is advanced forwardly into the barrel, the medication is injected through the needle and into a patient. At the completion of the injection stroke, the cartridge engages a needle retainer to actuate needle retraction. The needle is subsequently retracted to shield the contaminated needle.

40 Claims, 19 Drawing Sheets

U.S. PATENT DOCUMENTS

| | | |
|---|---|---|
| 4,315,570 A | 2/1982 | Silver et al. |
| 4,405,317 A | 9/1983 | Case |
| 4,413,991 A | 11/1983 | Schmitz et al. |
| 4,424,057 A | 1/1984 | House |
| 4,581,016 A | 4/1986 | Gettig |
| 4,693,706 A | 9/1987 | Ennis, II |
| 4,702,737 A | 10/1987 | Pizzino |
| 4,738,660 A | 4/1988 | Lucas |
| 4,755,169 A | 7/1988 | Sarnoff et al. |
| 4,861,335 A | 8/1989 | Reynolds |
| 4,883,471 A | 11/1989 | Braginetz et al. |
| 4,979,941 A | 12/1990 | Ogle, II |
| 5,069,670 A | 12/1991 | Vetter et al. |
| 5,114,411 A | 5/1992 | Haber et al. |
| 5,281,198 A | 1/1994 | Haber et al. |
| 5,360,410 A | 11/1994 | Wacks |
| 5,364,369 A | 11/1994 | Reynolds |
| RE34,845 E | 1/1995 | Vetter et al. |
| 5,489,267 A | 2/1996 | Moreno et al. |
| 5,520,642 A | 5/1996 | Bigagli et al. |
| 5,531,683 A | 7/1996 | Kriesel et al. |
| 5,599,312 A | 2/1997 | Higashikawa |
| 5,637,087 A | 6/1997 | O'Neil et al. |
| 5,641,010 A | 6/1997 | Maier |
| 5,685,846 A | 11/1997 | Michaels, Jr. |
| 5,720,731 A | 2/1998 | Aramata et al. |
| 5,769,825 A | 6/1998 | Lynn |
| 5,891,087 A | 4/1999 | Ohtani et al. |
| 5,899,881 A | 5/1999 | Grimard et al. |
| 6,228,065 B1 | 5/2001 | Lynn |
| 6,723,068 B2 * | 4/2004 | Lavi et al. .................... 604/82 |

FOREIGN PATENT DOCUMENTS

| | | |
|---|---|---|
| WO | WO 00/12160 | 3/2000 |
| WO | WO 00/29049 | 5/2000 |

* cited by examiner

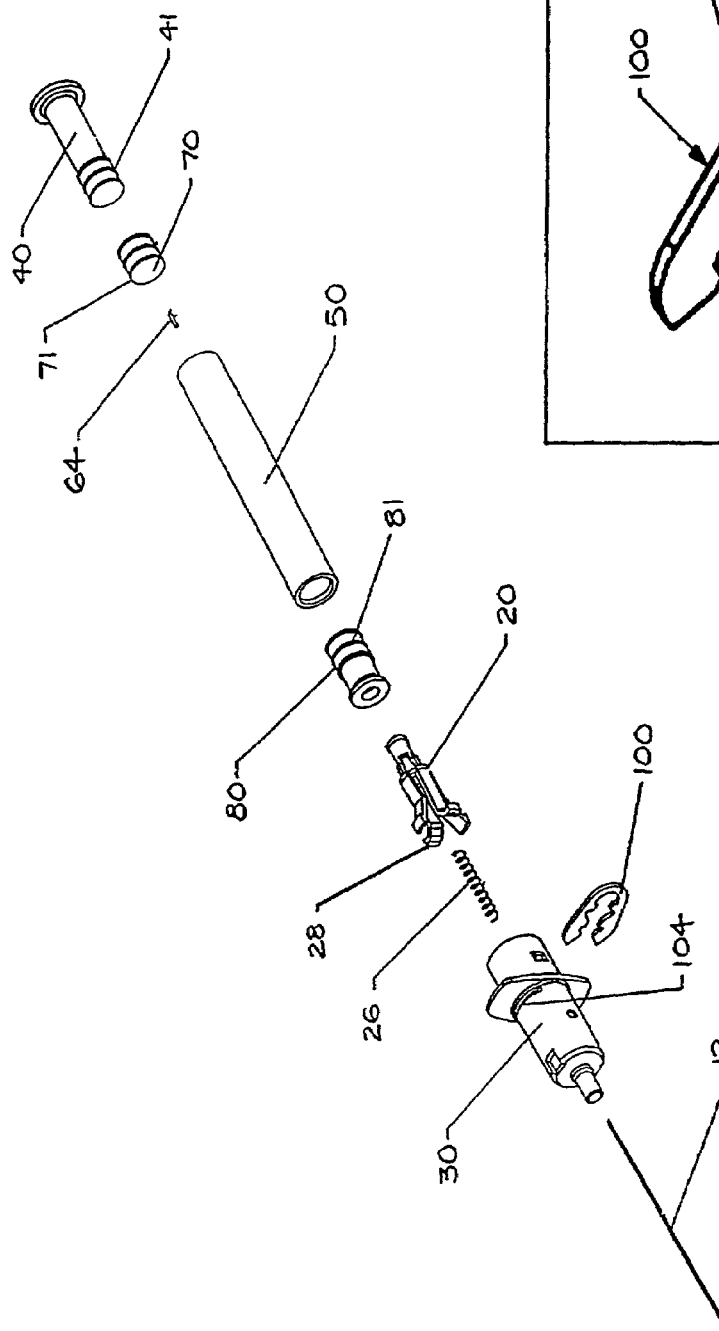

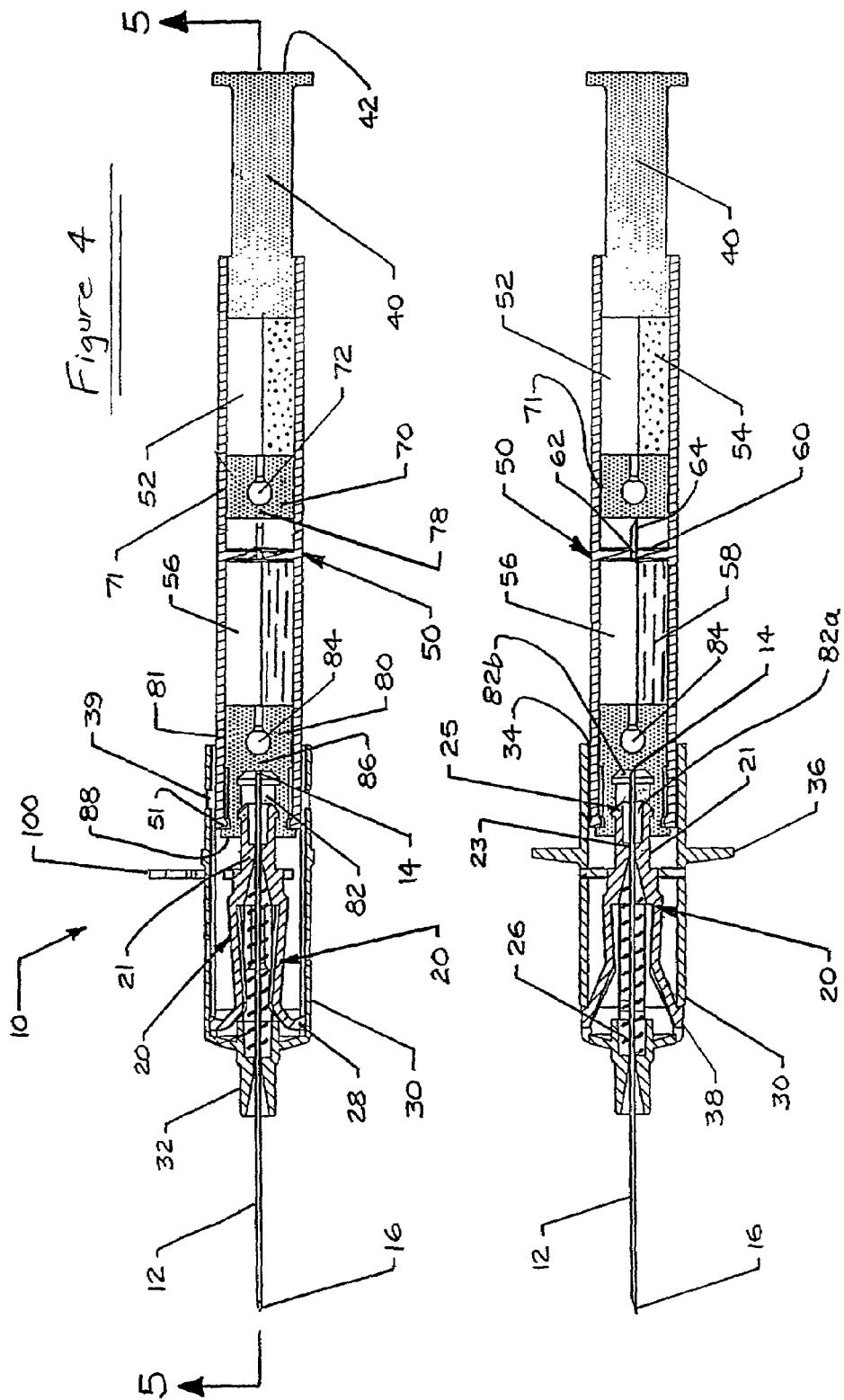

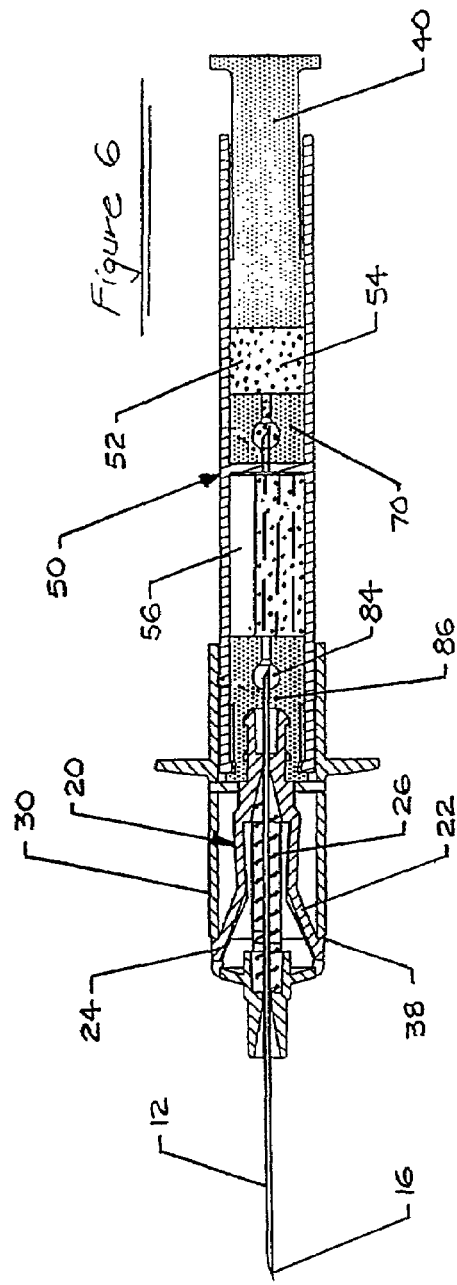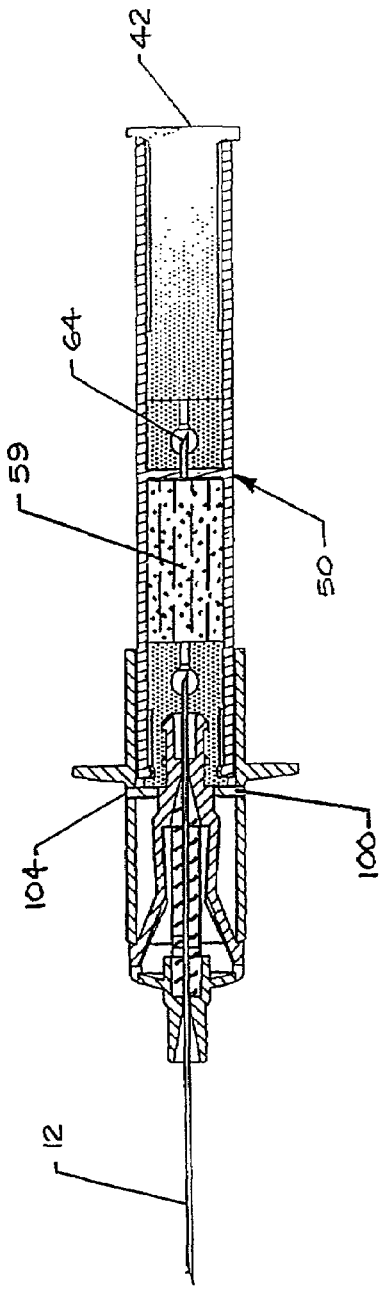

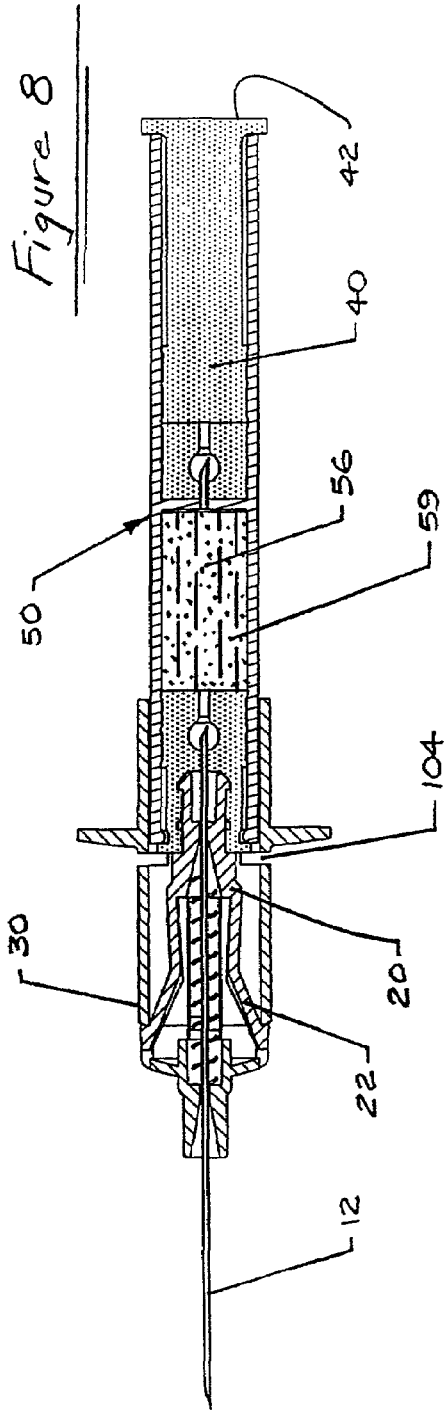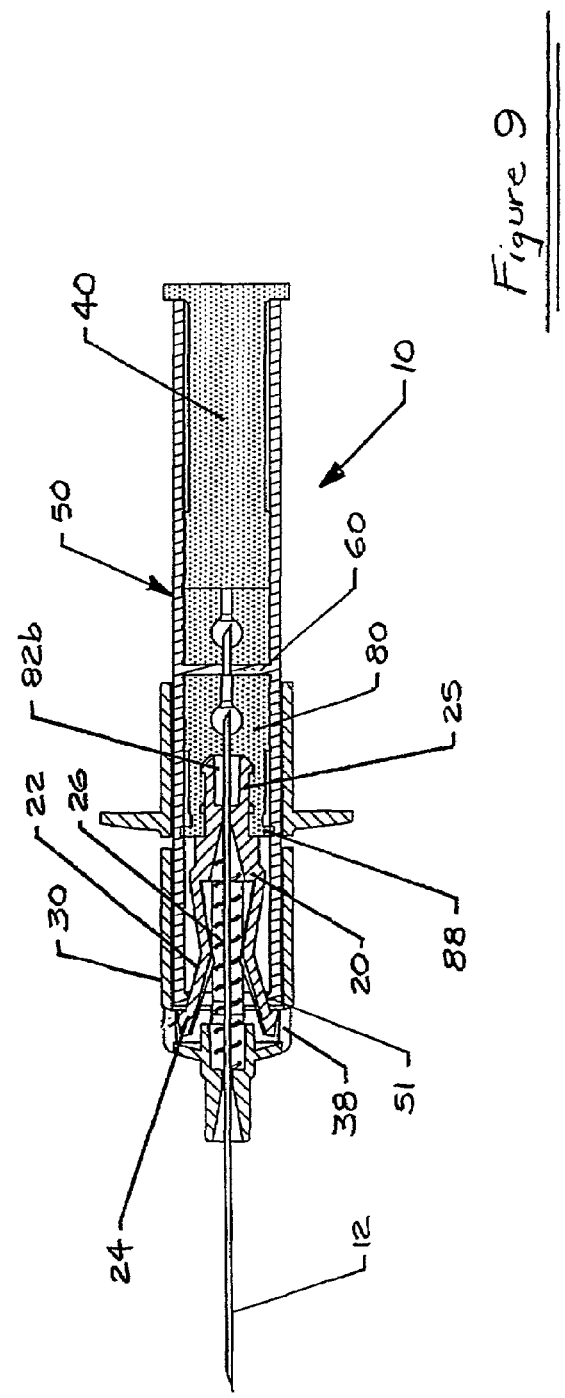

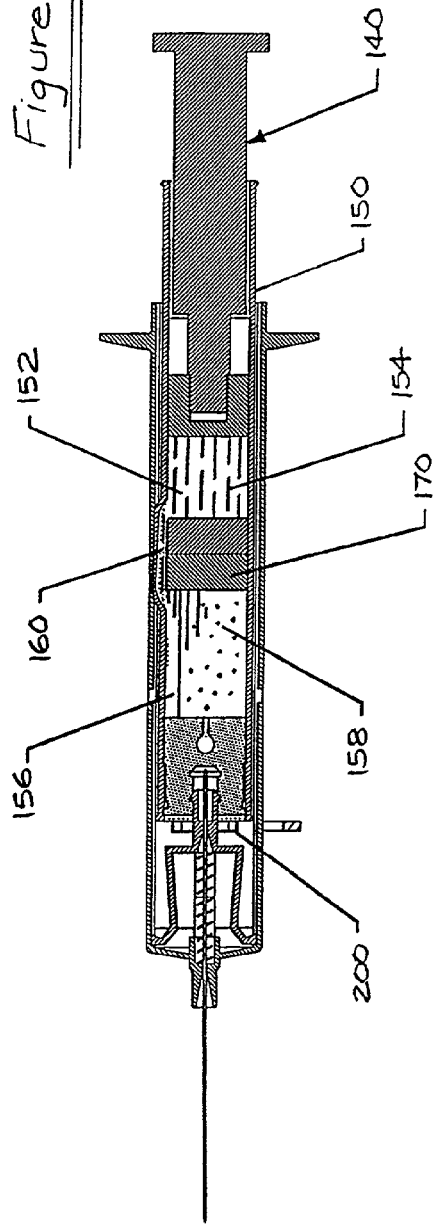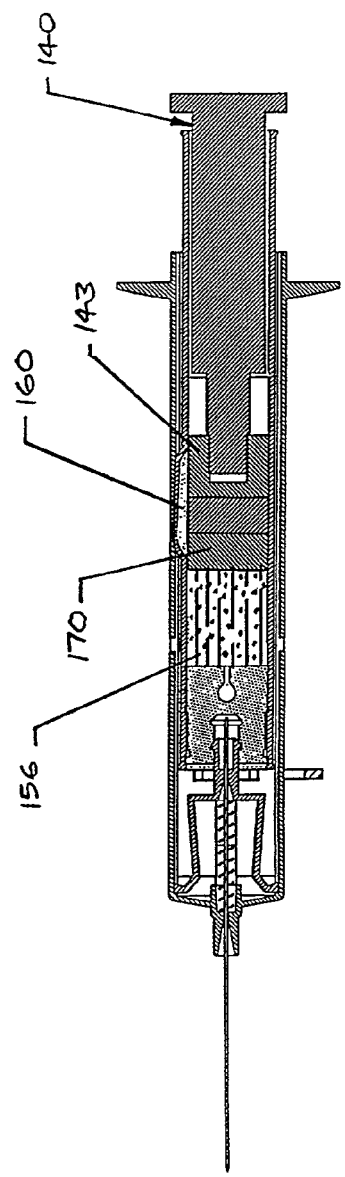

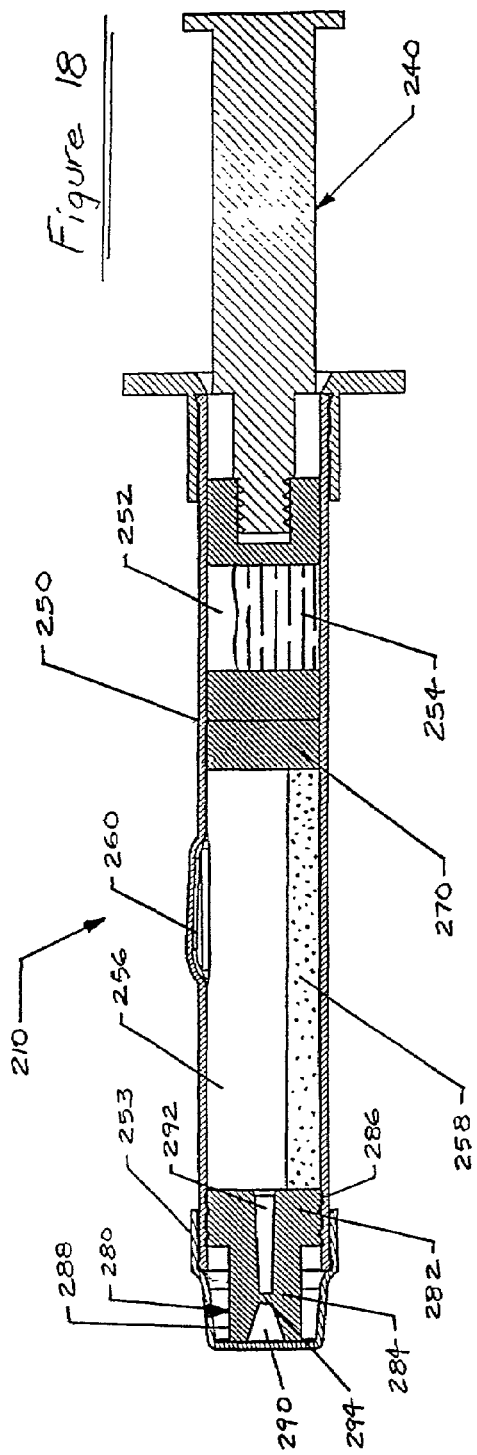
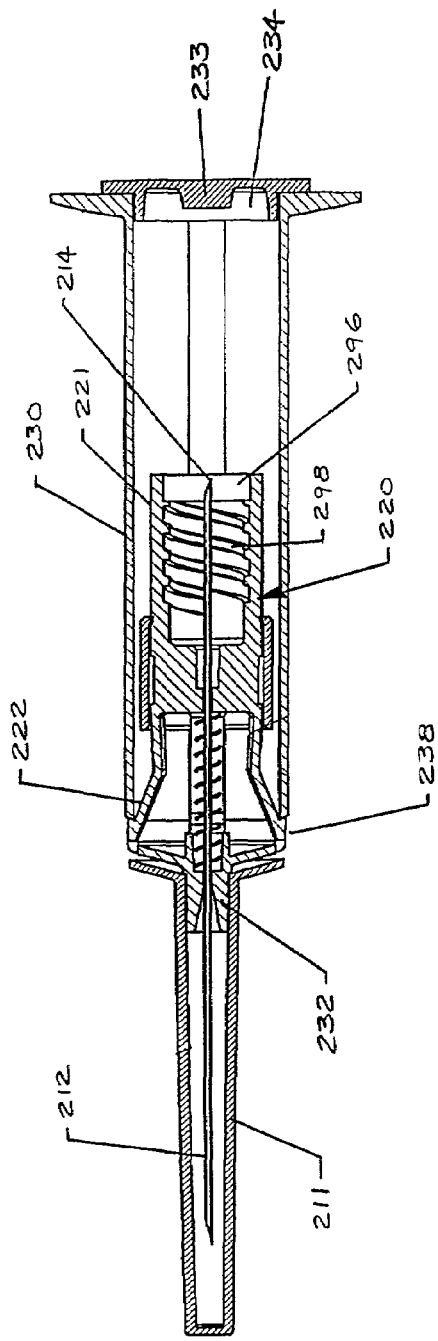

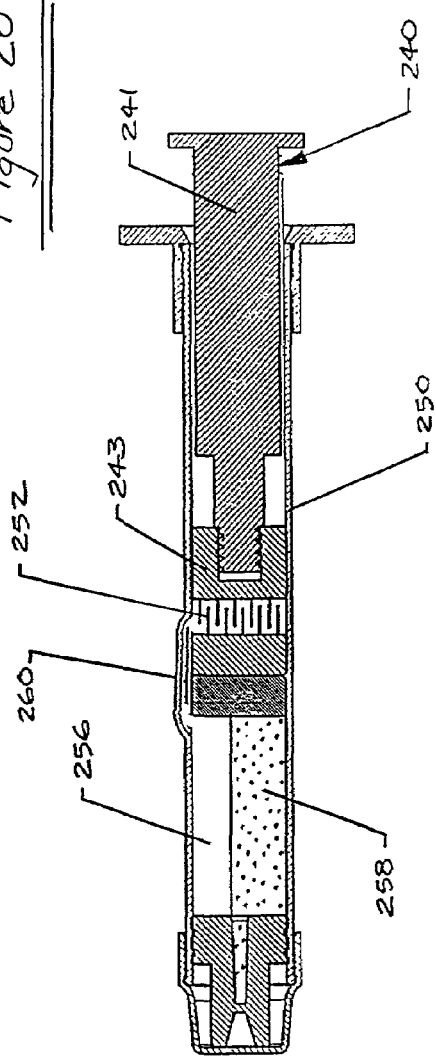
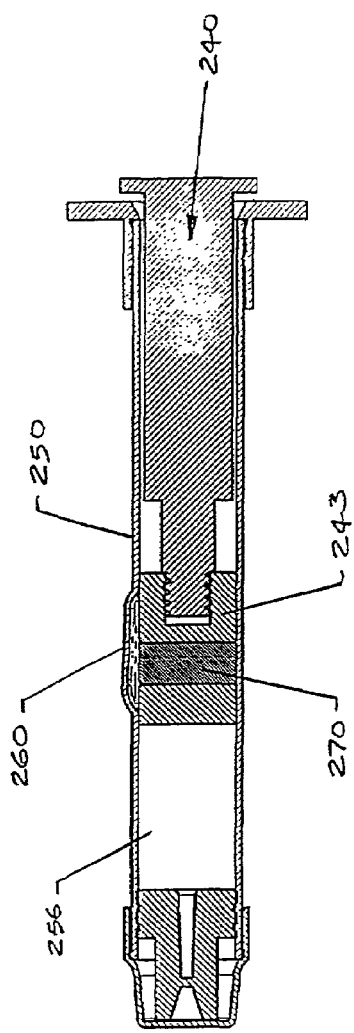

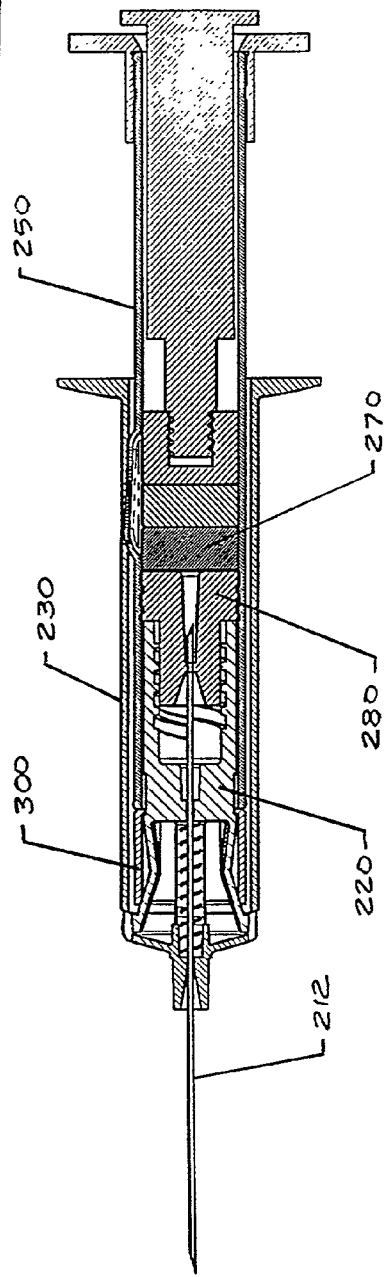
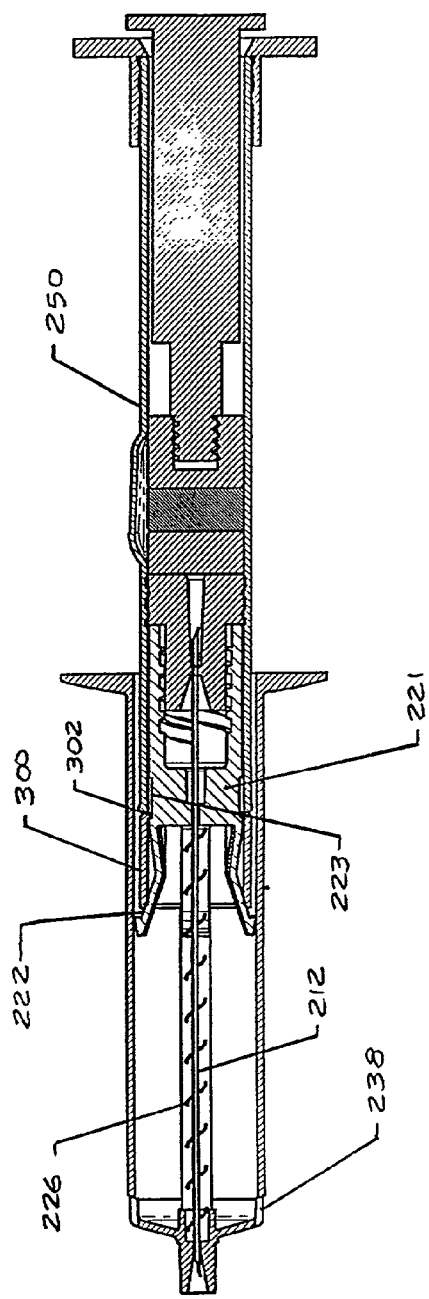

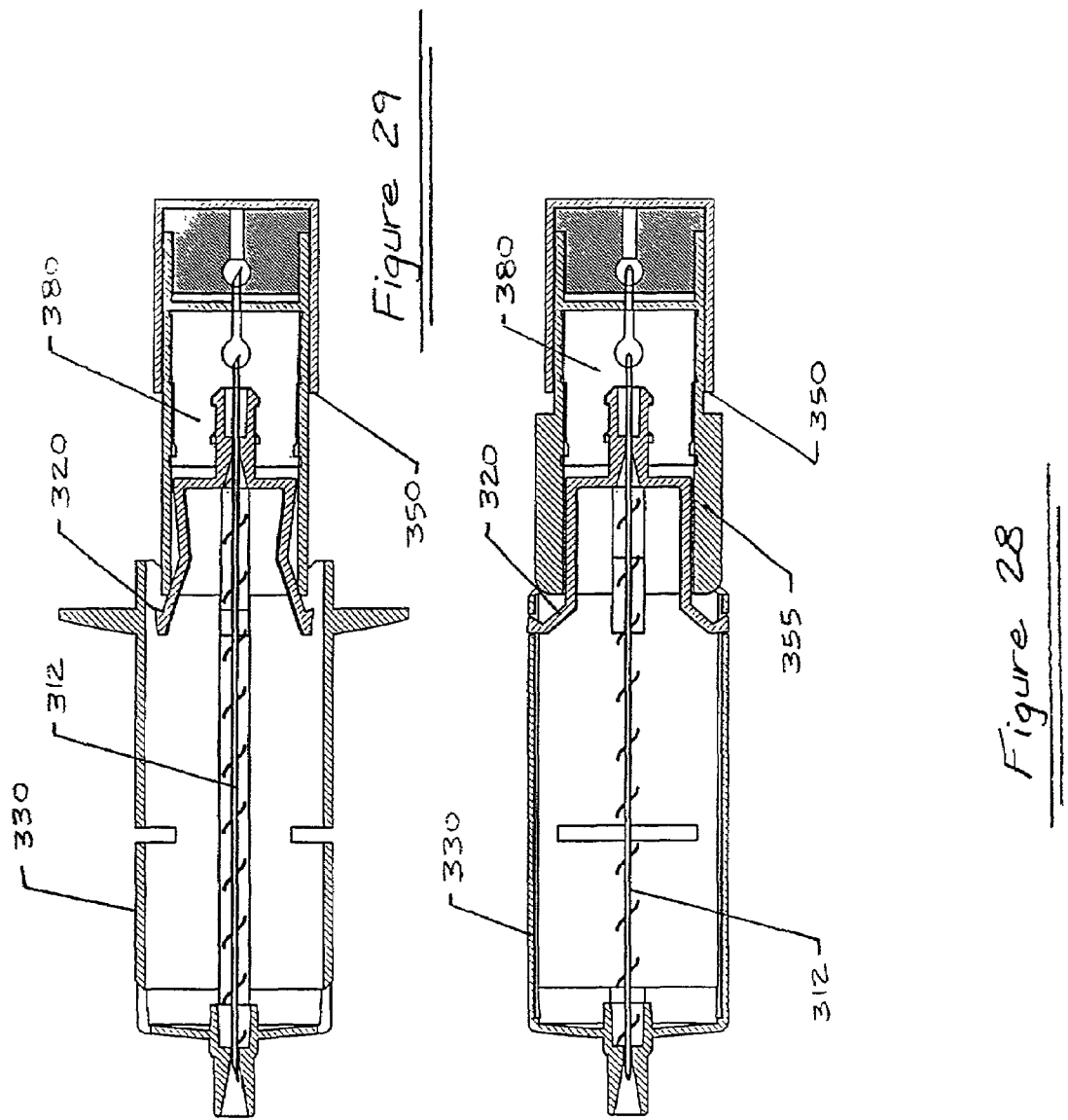

ND INJECTOR

PRIORITY CLAIM

This application claims priority to U.S. Provisional Application No. 60/275,568, filed Mar. 13, 2001, which is hereby incorporated herein by reference.

FIELD OF THE INVENTION

The present invention relates to medical devices and more particularly to medical devices having a cartridge with two chambers that store separate components of a medication and allow the components to be mixed and subsequently injected into a patient.

BACKGROUND

Pre-filled syringes store and allow for mixing of separate medicinal components. Many of these syringes, sometimes called "mixing syringes," store a first component in one compartment and a diluent or a second component in a second compartment. These syringes allow the two components to be stored separately until just before the syringe is used, at which time the components can be mixed within the syringe and immediately injected into a patient.

Pre-filled mixing syringes are advantageous for many types of pharmaceuticals. Some medications, like antibiotics, vitamins and hormones, must be packaged and stored in component parts to enhance shelf life. These medications may need to be stored as a powdered component and a diluent, or as a separate pair of solutions. Pre-filled mixing syringes allow medications to be stored in component parts right up until the medication is injected. In addition, pre-filled mixing syringes eliminate the burden of measuring medicinal components and mixing diluents from separate containers.

Despite these advantages, prior mixing syringes have not offered reliable safety features to protect the syringe user from accidental needle sticks following injection. In particular, prior syringe assemblies have not provided a mixing syringe that operates integrally with an injection needle that can be automatically shielded upon completion of the injection.

SUMMARY OF THE INVENTION

With the foregoing in mind, the present invention provides a pre-filled medical device for mixing separate components of a medication and injecting the medication into a patient. The device includes a two-chambered container, such as a cartridge, connected to a needle that retracts automatically after use. After retraction, the contaminated needle tip is enclosed within the device to prevent inadvertent needle sticks.

The device includes a hollow barrel surrounding the needle and having a generally open rearward end that forms a socket. A two-chambered cartridge containing component parts of a medication is adapted to engage the socket. Prior to use, the components are stored separately in the two cartridge chambers. During use, a plunger disposed in the rearward end of the cartridge is advanced into the cartridge to combine the two components in one chamber for mixing. Subsequent pressure on the plunger advances the medicinal mixture through the needle into a patient.

The injection needle is operable between an extended position and a retracted position. In the extended position, the forward tip of the needle projects forwardly from the barrel. In the retracted position, the forward tip is enclosed within the barrel. When the needle is in the extended position, a biasing element biases the needle toward the retracted position. A needle retainer releasably retains the needle in the extended position against the force of the biasing element. During the injection stroke, the cartridge disengages the needle retainer to allow the biasing element to propel the needle rearwardly into the barrel.

DESCRIPTION OF THE DRAWINGS

The foregoing summary as well as the following detailed description of the preferred embodiments will be best understood when read in conjunction with the following drawings, in which:

FIG. 2 is an exploded perspective view of the cartridge injector shown in FIG. 1;

FIG. 3 is an enlarged view of a locking clip of the cartridge injector shown in FIG. 2;

FIG. 4 is a sectional view of the cartridge injector shown in FIG. 1 taken along the line 4—4;

FIG. 5 is a sectional view of the cartridge injector shown in FIG. 4 taken along the line 5—5;

FIG. 6 is a sectional view of the cartridge injector shown in FIG. 1, illustrating the device prior to mixing the component parts of the medication;

FIG. 7 is a sectional view of the cartridge injector shown in FIG. 1, illustrating the device after mixing with the cartridge locked to impede injection;

FIG. 8 is a sectional view of the cartridge injector shown in FIG. 1, illustrating the device after mixing the cartridge unlocked to allow injection;

FIG. 9 is a sectional view of the cartridge injector shown in FIG. 1, illustrating the device, after injection, just prior to needle retraction;

FIG. 14 is a sectional view of the device shown in FIG. 12 illustrating the device during mixture of the medicinal components in the cartridge transfer of one component of medicine between chambers.

FIG. 15 is a sectional view of the device shown in FIG. 12 illustrating the device after mixture of the medicinal components.

FIG. 18 is a sectional view of the cartridge portion of the device illustrated in FIG. 17.

FIG. 19 is a sectional view of the device shown in FIG. 17 illustrated without the cartridge, illustrated prior to use.

FIG. 20 is a sectional view of the cartridge in FIG. 18 illustrating the device during mixture of the medical components.

FIG. 21 is a sectional view of the device shown in FIG. 18 illustrating the device after mixture of the medical components.

FIG. 22 is a sectional view of the device shown in FIG. 17 illustrating the device at the completion of an injection.

FIG. 23 is a sectional view of the device shown in FIG. 17 illustrating the device after needle retraction.

FIG. 28 is a sectional view of the device shown in FIG. 24 illustrating the device after needle retraction.

FIG. 29 is a sectional view of the device shown in FIG. 24 illustrating the device after needle retraction.

DETAILED DESCRIPTION OF THE PREFERRED EMBODIMENTS

Figure 1:
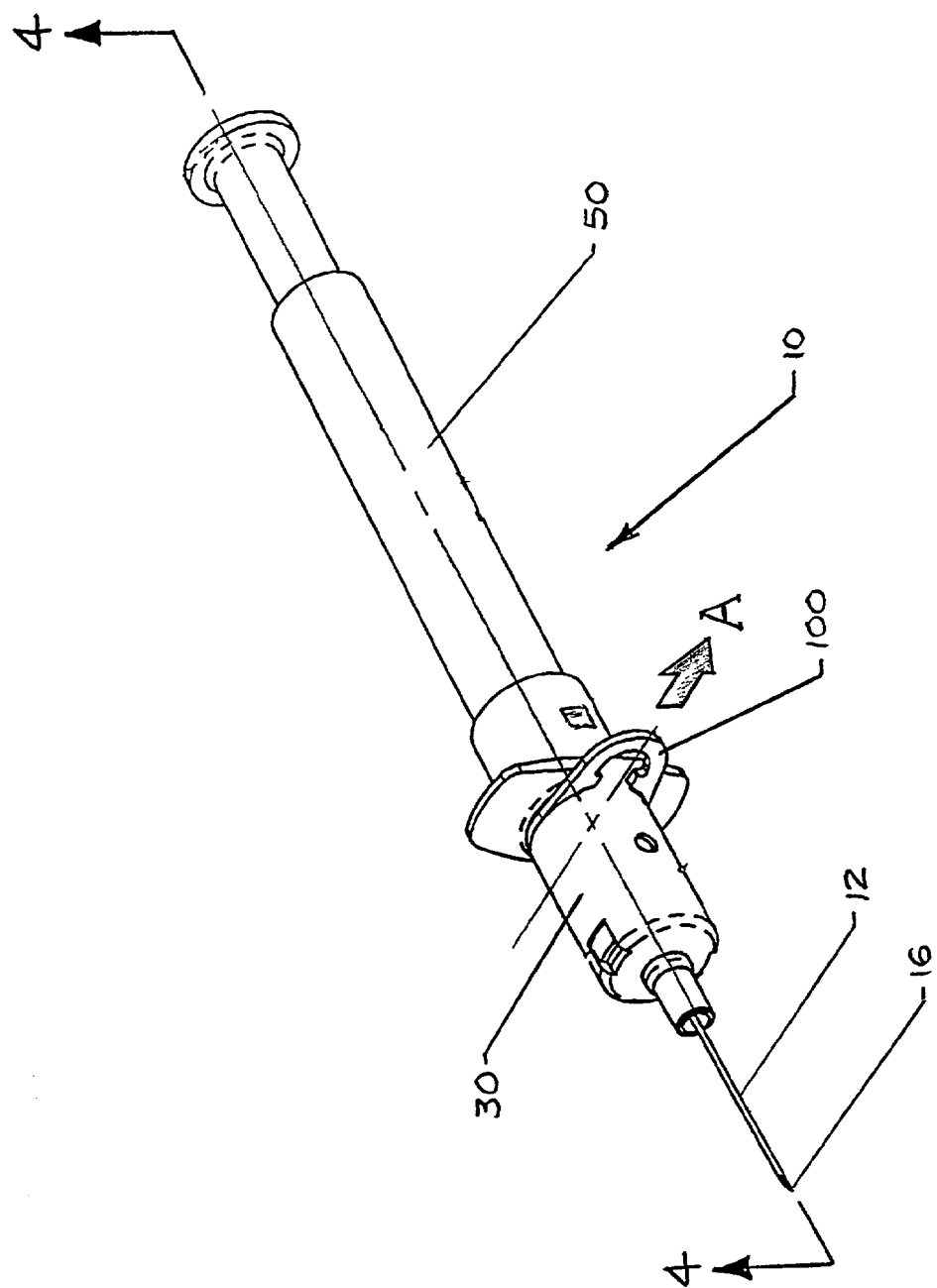
FIG. 1 is perspective view of a pre-filled cartridge injector having a two-chambered container that stores component parts of a medication.

Referring now to the figures in general, and to FIGS. 1–11 specifically, an injector device 10 is shown with a needle 12 having a sharpened distal tip 16 for insertion into a patient. As shown in FIG. 4, the injector device 10 has an attached cartridge 50 having a first chamber 52 and a second chamber 56. The two chambers 52, 56 are pre-filled with component parts of a medication that are to be mixed prior to injection. The cartridge 50 also includes a plunger 40 that is slidable within the cartridge. Initially, advancing the plunger 40 in the cartridge 50 expels the medicinal component from the first chamber 52 into the second chamber 56 to mix the two medicinal components. After mixing the components, advancing the plunger drives the cartridge forwardly to inject the medicine into a patient. Upon completion of the injection stroke, the medical professional releases pressure from the plunger to allow automatic retraction of the needle 12 into the device 10 to protect the contaminated needle 12 from inadvertent contact.

The injector device 10 includes a double-ended needle 12, a generally cylindrical barrel 30, a compression spring 26 and a needle retainer 20 releasably retaining the needle against the bias of the spring. As shown in FIGS. 4 and 5, the needle 12 has a sharpened proximal tip 14 and a sharpened distal tip 16. The spring 26 circumscribes the needle 12 and is compressed against the interior of the barrel 30 at the barrel's distal end. The rearward end of the spring 26 bears against the interior of the needle retainer 20 to bias the needle 12 and needle retainer in the rearward direction.

Figure 10:
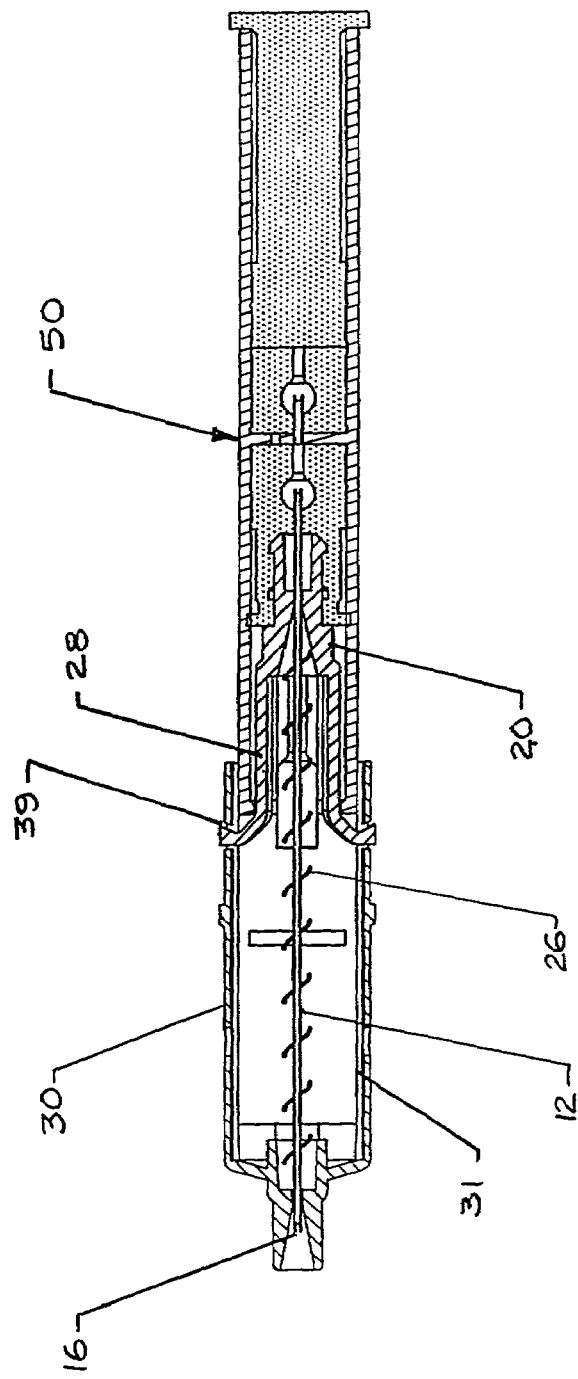
FIG. 10 is a sectional view of the cartridge injector shown in FIG. 1, illustrating the device after needle retraction.

The needle 12 is operable between two positions, an extended position and a retracted position. In the extended position, the needle 12 projects forwardly from the forward end of the barrel 30. In the retracted position, the needle 12 is retracted into the barrel 30 so that the sharpened tip 16 of needle 12 is enclosed within the barrel to prevent inadvertent contact with the sharpened tip. When the needle is in the extended position, the spring 26 biases the needle 12 rearwardly toward the retracted position. The needle retainer 20 releasably retains the needle 12 in the extended position, against the bias of the spring 26. During the injection stroke, the cartridge 50 cooperates with the needle retainer 20 to allow the needle to retract into the barrel 30, as shown in FIG. 10.

Referring now to FIGS. 5–7, the cartridge 50 includes a first chamber 52 containing a first medicinal component 54 and a second chamber 56 containing a second medicinal component 58. The chambers 52, 56 are separated by a mid wall 60 containing an orifice 62. A rear seal 70 seals the first chamber 52 to prevent the components from being mixed prior to use. When the rear seal 70 is pierced and the plunger 40 is advanced into the cartridge 50, the first component 54 flows into the second chamber 56 through the orifice 62, where it combines with the second component 58 to form the medication 59, as shown in FIGS. 6–7. Subsequent pressure on the plunger 40 and cartridge 50 forces the medication 59 through the needle 12 and into the patient.

Referring now to FIGS. 4–6, the elements of the injector device 10 will be described in greater detail. The barrel 30 is generally cylindrical and the distal end of the barrel has a tapered nose 32. The nose 32 has an opening through which the needle 12 extends so that the sharpened tip 16 of the needle can be inserted into a patient. The rearward end of the barrel 30 is open, forming a cylindrical socket 34 adapted to receive the cartridge 50. Two laterally extending flanges 36 project outwardly from the barrel 30, transverse the longitudinal axis of the barrel, forming a pair of finger grips for operating the device 10. The barrel 30 further includes a pair of retaining apertures 38 and a pair of lockout windows 39 that cooperate with the needle retainer 20 as described further below.

As shown in FIG. 5, a hub 21 projects from the rearward end of the needle retainer 20. The hub 21 is a generally cylindrical element having a central bore 23. The needle 12 is disposed within the central bore 23 of the hub 21 so that the rearward end 14 of the needle 12 projects rearwardly from the hub and the forward end 16 of the needle projects forwardly from the hub. The needle 12 can be attached to the hub 21 in one of several ways. For example, the needle 12 can be attached to the hub 21 by an adhesive such as a UV curable adhesive. Alternatively, the needle 12 can be molded into the hub 21, which is formed of plastic. The rearward end of the hub 21 includes a circumferentially barbed connector 25 configured to cooperate with the cartridge 50 to connect the cartridge to the needle hub 21 as discussed further below.

The needle retainer 20 is axially displaceable within barrel 30 to facilitate needle retraction. The needle retainer 20 can be molded out of a rigid, high strength resin, such as polycarbonate. Prior to retraction, the needle retainer 20 is maintained in a fixed axial position while the medication 59 is expelled from the cartridge 50. After the injection, the needle retainer 20 and the attached needle 12 are displaced rearwardly by the compression spring 26.

The spring 26 is a compression spring and may be formed of stainless steel, treated carbon steel wire or other suitable non-corrosive spring metal. The residual compression of the spring prior to disengagement of the needle retainer is of sufficient magnitude to facilitate complete needle retraction and overcome the frictional resistance between sliding components within the device 10.

Referring now to FIG. 6, the needle retainer 20 includes a pair of retaining arms 22 that extend radially outwardly and forwardly from the distal end of the needle retainer 20. During operation, the needle retainer 20 is operable between a locked position and an unlocked position. In the locked position, the retaining arms 22 engage the retaining apertures 38 in the barrel wall to maintain the needle in a fixed axial position with the forward tip 16 of needle 12 projecting forwardly from the barrel 30. More specifically, in the locked position, the retaining arms 22 engage the barrel 30 to hold the needle hub 21 and needle 12 against the rearward bias of the spring 26. In the unlocked position, the retaining arms 22 are positioned so as to allow the needle hub 21 and needle 12 to be retracted rearwardly. More specifically, in the unlocked position, the retaining arms 22 are disengaged from the retaining apertures 38, allowing the spring 26 to propel the needle hub 21 and needle 12 rearwardly.

As discussed above, the retaining arms 22 on the needle retainer 20 project forwardly and outwardly into engagement with the retaining apertures 38 in the wall of the barrel 30. The terminal end of each arm forms a retaining tab 24 that is configured to project into a retaining aperture 38. More specifically, the retaining tabs 24 engage the lip formed by each retaining aperture 38 in the wall of the barrel 30. In this way, the retaining tabs 24 operate as a pair of latches to retain the needle hub 21 and needle 12 against the rearward bias of the spring.

Referring again to FIGS. 4 and 5, the cartridge 50 is a generally cylindrical vessel that may be molded out of pharmaceutical quality glass such as borosilicate, or a rigid inert plastic such as polyolefin or polyester. The midwall 60 that separates the first and second chambers may be formed of a rigid inert plastic such as polyolefin or polyester. The barrier or midwall 60 can be molded as part of the cartridge 50 or bonded to the inside wall of the cartridge. Each chamber is filled with a predetermined amount of a medication during manufacturing of the device 10.

The front end of the forward chamber 56 is sealed by an elastomeric front seal 80, which may be molded in a self-sealing biocompatible elastomer such as polyisoprene. The front seal 80 is generally cylindrical, having a plurality of axially-spaced circumferential ribs 81. The ribs 81, which are more clearly shown in FIG. 2, frictionally and sealingly engage the interior of the container to provide a fluid tight seal, thereby preventing fluid from leaking from the cartridge 50. The front seal 80 also has a front end that is pierceable by the rearward sharpened tip 14 of needle 12. After being pierced, the front end of the front seal 80 reseals around the needle 12 to prevent fluid from leaking from the cartridge 50.

Referring now to FIGS. 5 and 6, the front seal 80 has a socket 82 configured to cooperate with the barbed connector 25 on the needle hub 21. The socket 82 includes two radially relieved recesses, 82a and 82b, that mate with the barbed connector 25. Specifically, the barbed connector 25 matingly engages the front seal 80 in a first position and a second position.

In the first position, the barbed connector 25 engages the first recess 82a, as shown in FIG. 5. In this position, the cartridge is attached to the hub, but the rearward end of the needle does not pierce the front seal 80. Applying pressure to the plunger 40 displaces the cartridge forwardly relative to the hub, thereby displacing the barb into to the second position. In the second position, the barbed connector 25 engages the second recess 82b, as shown in FIG. 6. In this position, the rearward end of the needle 12 pierces the front seal 80.

The front seal 80 includes a hollowed cavity 84 at its rearward end. In this way, a pierceable wall 86 is formed in the front seal 80 between the cavity 84 and the second recess 82b. As shown in FIG. 5 prior to use, the cartridge 50 is mounted in the first position so that the barbed connector 25 engages the first recess 82a. In this position, the needle 12 does not penetrate the pierceable wall 86. As the hub 21 is displaced from the first position to the second position, the rearward end 14 of the needle 12 pierces the wall 86 and extends into the cavity 84 as shown in FIG. 6. The cavity 84 opens into the interior of the second chamber 56 of cartridge 50 so that when the needle 12 projects into the hollowed section 84, the needle is in fluid communication with the interior of the cartridge. After the needle 12 penetrates the pierceable wall 86, the wall reseals around the needle to form a fluid-tight seal and prevent medication in the cartridge 50 from leaking around the needle.

To prepare the injection device 10 for use, the medical professional displaces the cartridge 50 forwardly relative to the needle retainer 20, so that the forward seal 80 is driven over the barbed connector 25, such that the barbed connector engages the second recess 82b. At the same time, the proximal tip 14 of needle 12 pierces the pierceable wall 86, so that the needle is in fluid communication with the second chamber, as shown in FIG. 6.

The connection between the front seal 80 and the needle hub 21 is preferably a one-way engagement. In other words, when the front seal 80 is mounted on the barbed connector 25, the cartridge 50 can be displaced forwardly relative to the barbed connector, but the cartridge cannot be displaced rearwardly relative to the barbed connector. In this way, the cartridge 50 cannot be readily removed from the needle hub 21 in barrel 30, such that the cartridge is substantially permanently attached to the needle hub and barrel.

The one-way connection is facilitated by the rearward-facing tapered shoulder of the barbed connector 25 and the square shaped forward-facing shoulder of the barbed connector. In particular, the rearward-facing shoulder of the barbed connector 25 cooperates with tapered sides in the first and second radial recesses 82a and 82b to permit relative displacement of the plug from the first recess to the second recess. Reverse displacement from the second recess 82b back to the first recess 82a is resisted by the square shaped forward-facing shoulders on barbed connector 25, which act to impede reverse displacement.

Referring now to FIG. 4, the front seal 80 is configured to prevent ejection of fluid when the barbed connector 25 is displaced from the first position, in which the barbed connector 25 engages the first radial recess 82a, to the second position, in which the barbed connector engages the second radial recess 82b. Specifically, the front seal 80 includes a flared head 88 or circumferential flange at the forward end of the front seal. The open distal end of the cartridge 50 terminates with a beaded rim 51 that seats against the rearward edge of the flared head 88. The outside diameter of the flared head 88 is greater than the inside diameter of the open distal end of the cartridge 50, thereby impeding rearward displacement of the front seal 80 into the cartridge when force is initially applied to the plunger 40. In addition, the force required to overcome the frictional engagement between the outer circumference of the front seal 80 and the inner wall of the cartridge 50 is greater than the force required to displace the plug 25 from the first recess 82a to the second recess 82b. Accordingly, when force is initially applied to the plunger 40, the front seal 80 remains in a fixed position relative to the cartridge 50, while the barbed connector 25 is displaced into the second position. This restriction on the front seal 80 limits the release of fluid from the cartridge 50 when the needle 12 pierces the wall 86.

During storage of the injection device 10, the medication is divided into two separate components stored in the cartridge 50, as shown in FIG. 5. Specifically, a first component 54 of the medicine is stored in the rear chamber 52 and a second component 58 of the medicine is stored in the forward chamber 56. The two chambers are separated by the mid-wall 60 containing an orifice 62 and a hollow piercing member 64 mounted in the orifice. The orifice 62 is located axially at the center of the midwall 60. In addition, a small vent hole 63 is located just off center in the midwall 60 to vent the air from the dead space area between the mid wall and the mid seal 70. Preferably, the piercing member 64 is fabricated out of suitable non-corrosive material such as stainless steel or treated carbon steel wire. When the plunger 40 is axially advanced in the cartridge 50, the first component 54 in the rear chamber 52 advances through the piercing member 64 and into the forward chamber 56 to combine with the second component 58.

Prior to use of the injection device 10, fluid communication between the first and second chambers is prevented by an elastomeric mid seal 70, which may be molded in a self-sealing biocompatible elastomer such as polyisoprene. The mid seal 70 is initially slidably disposed in the first chamber 52 between the piercing member 64 and the first component 54, as shown in FIGS. 4–5. The mid seal 70 is generally cylindrical, having a plurality of axially-spaced circumferential ribs 71, as shown more clearly in FIG. 2. The ribs 71 frictionally and sealingly engage the inner wall of the cartridge 50 to provide a fluid-tight seal. This fluid-tight seal prevents fluid in the first chamber from entering the piercing member 64. The mid seal 70 also includes a hollowed section 72 formed in the forward end of the mid seal that opens to the first chamber 52 at the rearward end of the mid seal. The forward end of the mid seal 70 is closed by a membrane 78 that is pierceable by the piercing member 64. Upon piercing the membrane 78, fluid communication is established between the first and second chambers to allow the first and second components of the medication to be mixed.

Like the front seal 80 and mid seal 70, the plunger 40 is generally cylindrical, preferably having a plurality of axially-spaced circumferential ribs 41. The plunger 40 may be molded in a self-sealing biocompatible elastomer such as polyisoprene. Alternatively, the plunger 40 could be a two-part assembly in which a cylindrical elastomeric seal is mounted to a rigid plastic plunger rod. The ribs 41, which are more clearly shown in FIG. 2, frictionally and sealingly engage the interior of the cartridge 50 to provide a fluid tight seal, thereby preventing fluid from leaking from the proximal end of the cartridge.

The plunger 40 is slidable within the first chamber 52 in response to pressure applied to the thumb pad 42. When the plunger 40 is axially advanced into the cartridge 50, the first component 54 is compressed against the rearward end of the mid seal 70 in the first chamber 52. As back pressure on the mid seal 70 overcomes the frictional resistance between the mid seal and the cartridge 50, the mid seal is displaced into the piercing member 64 until the membrane 78 is pierced, as shown in FIG. 6. As the mid seal advances, air from the space between the mid seal and mid wall vents through the vent hole 63 in the mid wall. At such time, the piercing member 64 penetrates through the hollowed section 72 to connect the first chamber 52 and second chamber 56 in fluid communication.

After the mid seal 70 is pierced, pressure applied to the plunger 40 advances the first component 54 through the piercing member 64 and into the second chamber 56 where the first and second components are subsequently mixed to form the medication 59. The plunger 40 is displaced forwardly relative to the first chamber 52 until the flanged portion of the thumb pad 42 contacts the proximal end of the cartridge 50, as shown in FIG. 7. The outside diameter of the thumb pad 42 is larger than the inside diameter of the cartridge 50, thereby preventing further displacement of the plunger 40 once the thumb pad contacts the proximal end of the cartridge 50. Preferably, the distance between the forward end of the plunger 40 and the rearward end of the mid seal 70 is equal to the distance between the flanged portion of the thumb pad 42 and the proximal end of the cartridge 50. Once the thumb pad 42 contacts the proximal end of the cartridge 50, the plunger is fixed relative to the cartridge 50. At this point, axial advancement of the cartridge 50 relative to the barrel 30 is restricted, as described in more detail below.

Preferably, the injection device 10 includes a locking mechanism for preventing accidental release of the contents in the second chamber prior to mixing the two components. In the present embodiment shown in FIG. 7, the barrel 30 includes a locking clip 100 in the barrel wall to prevent accidental discharge of the medicinal components. The wall of the barrel 30 includes a pair of radial slots 104 formed in a plane that is transverse the longitudinal axis of the barrel. When the locking clip 100 is inserted through the slots 104, the clip prevents inadvertent forward displacement of the cartridge 50 relative to the front seal 80, thereby preventing accidental advancement of the medicinal components through the needle 12. The locking clip 100 is preferably formed of a resilient high strength and high modulus resin, such as acetyl or polycarbonate, and is configured to releasably engage the slots 104 in the barrel 30.

Referring to FIGS. 1–3, the locking clip 100 is preferably a flat member having a pair of resiliently deflectable legs 101 that join to form a U-shape. The open end of the locking clip 100 has tapered edges 102 that allow the legs 101 to deflect outwardly as the locking clip 100 is inserted into the sidewall of the barrel 30. In addition, the locking clip 100 has a plurality of teeth 103 on the inside edge of the legs 101 that are adapted to engage the edges of radial slots 104.

As the locking clip is inserted into the sidewall of the barrel 30, the legs 101 deflect outwardly to allow the teeth 103 to clear the edges of radial slots 104. Upon being deflected outwardly, the resilience of legs 101 bias the legs radially inwardly toward their original position. Once the teeth 103 are disposed within the slots 104, the legs 101 deflect radially inwardly toward their original position and releasably engage the outer edges of the needle retainer 20 in barrel 30. In the inserted position, the closed end of the locking clip 100 remains outside the barrel 30, as shown in FIGS. 1 and 4.

After the medicinal components are mixed within the cartridge, the locking clip 100 is removed to permit injection of the medicine 59, as shown in FIG. 8. The locking clip 100 is removed from the barrel 30 by pulling the closed end of the clip in a direction transverse to the longitudinal axis of the barrel. This direction is marked "A" in FIG. 1. By pulling the clip in this manner, the legs 101 are deflected outwardly from the slots 104 to allow the teeth 103 to clear the edges of slots 104.

After the locking clip 100 is removed from the barrel 30, the medication 59 is injected into the patient by advancing the cartridge forwardly into the barrel. Pressure applied to the thumb pad 42 causes the plunger 40 and cartridge 50 to move forwardly relative to the barrel 30. With the barbed connector 25 mounted in the second recess 82b in the front seal 80, the front seal remains stationary while the cartridge 50 is advanced forwardly, as shown in FIG. 9. The front seal 80 and flared head 88 are configured to form a sliding fit with the interior of the cartridge 50 so that the cartridge can slide over the front seal. As the cartridge 50 is advanced, the mid seal 70 and the mid wall 60 are displaced toward the front seal 80. This causes a reduction of volume in the second chamber 56, whereby the medication is displaced into the needle to facilitate the injection. At the completion of the injection, the mid wall 60 bears against the rearward end of the front seal 80, as shown in FIG. 9.

Referring now to FIGS. 9–10, the automatic retraction of the needle 12 shall be described. The cartridge 50 is axially advanced to the proximal end of the barrel 30 until the medication 59 is completely expelled from the second chamber 56. As the cartridge 50 is advanced, the beaded circumferential rim 51 of the cartridge is displaced into engagement with the retaining arms 22 of needle retainer 20. Preferably, the cartridge 50 is configured so that the longitudinal distance between the rearward end of the front seal 80 and the mid wall 60 corresponds to the longitudinal distance between the circumferential rim 51 of the cartridge and the retaining arms 22 when the cartridge is mounted on the barbed connector 25 in the second position. In this way, the rim 51 of the cartridge 50 engages the retaining arms 22 when substantially all of the medication 59 is expelled from the device 10.

After the rim 51 of cartridge 50 engages the retaining arms 22, continued axial advancement of the cartridge deflects the retaining arms radially inwardly so that the retaining tabs 24 are displaced inwardly, as shown in FIG. 9. In the inward position, the retaining tabs 24 are disengaged from the retaining apertures 38 of the barrel 30. In this way, the cartridge 50 operates as an actuator, such that axial advancement of the cartridge displaces the needle retainer 20 into an unlocked position. In the unlocked position, the needle retainer 20 is no longer locked in place against the force of the spring 26. After the needle retainer 20 is in the unlocked position and the user releases pressure on the plunger 40, the spring 26 propels the needle 12 rearwardly until the sharpened distal tip 16 of the needle is enclosed within the barrel 30.

As shown in FIG. 10, when the needle 12 is retracted, the needle, needle retainer 20 and cartridge 50 are displaced rearwardly together. During retraction, the retaining arms 22 are biased radially outwardly so that the retaining tabs 24 ride along the inside wall of the barrel. The force of the spring 26 is sufficiently strong to overcome the frictional resistance generated between the guide arms 28 and the barrel 30.

Preferably, the injection device 10 includes a mechanism for limiting rearward displacement of the retracted elements. Referring now to FIGS. 2, 4 and 10, the needle retainer 20 includes a pair of guide arms 28 that cooperate with a pair of alignment channels or grooves 31 formed in the interior wall of the barrel 30. The guide arms 28 may be molded out of a rigid, resilient high strength resin, such as polycarbonate. The guide arms 28 extend forwardly from the needle retainer 20 and project radially outwardly into engagement with the alignment grooves 31.

Each guide arm 28 includes a linear elongated rear portion which preferably is generally parallel to the longitudinal axis of barrel 30. The forward portion of each guide arm 28 bends outwardly transverse to the longitudinal axis of the barrel 30 and extends into one of the alignment grooves 31. When the needle retainer 20 is disposed within the barrel, the guide arms 28 are deflected radially inwardly from their natural state. In this position, the guide arms 28 are biased radially outwardly against the inner wall of the barrel 30 due to the resilient properties of the guide arms.

The forward ends of guide arms 28 are preferably contained within the alignment grooves 31 to substantially limit rotation of the needle and needle retainer 20 during needle retraction. This engagement ensures that the guide arms are aligned with the lockout windows 39 so that the guide arms snap into the lockout windows at the end of retraction. In this way, the needle retainer 20 is limited to axial displacement during needle retraction. During retraction, the frictional resistance between the forward ends of the guide arms 28 and the inside wall of the barrel 30 is overcome by the expansion force of the spring 26.

As shown in FIG. 4, the linear elongated rear portion of each guide arm 28 is spaced radially inwardly from the inner wall of the barrel 30 to create a clearance space between the linear portion of the guide arms and the barrel. Preferably, the minimum radial thickness of the clearance space is greater than the thickness of the wall of the cartridge 50 or the cartridge rim 51. In this way, when the cartridge 50 is advanced forwardly to disengage the retaining arms 22, advancement of the cartridge will not be impeded by the guide arms 28.

Each alignment groove 31 is substantially parallel to the longitudinal axis of the barrel 30. In FIG. 4, the groove 31 is shown extending to rearward end of the barrel. However, it may be desirable to terminate the groove forward of the rearward end of the barrel. The rearward portion of each alignment groove 31 intersects a lockout window 39 formed in the wall of the barrel 30. The lockout windows 39 are adapted to receive the forward ends of the guide arms 28, as shown in FIG. 10. In particular, as the front end of each guide arm 28 aligns with the corresponding lockout window 39 during needle retraction, the radially outward bias of the guide arm displaces the arm outwardly so that the forward end projects into the lockout window. The engagement between the guide arms 28 and lockout windows 39 prevent further axial movement of the retainer 22. As a result, the retracted elements are limited from further displacement in the forward or rearward direction.

Figure 11:
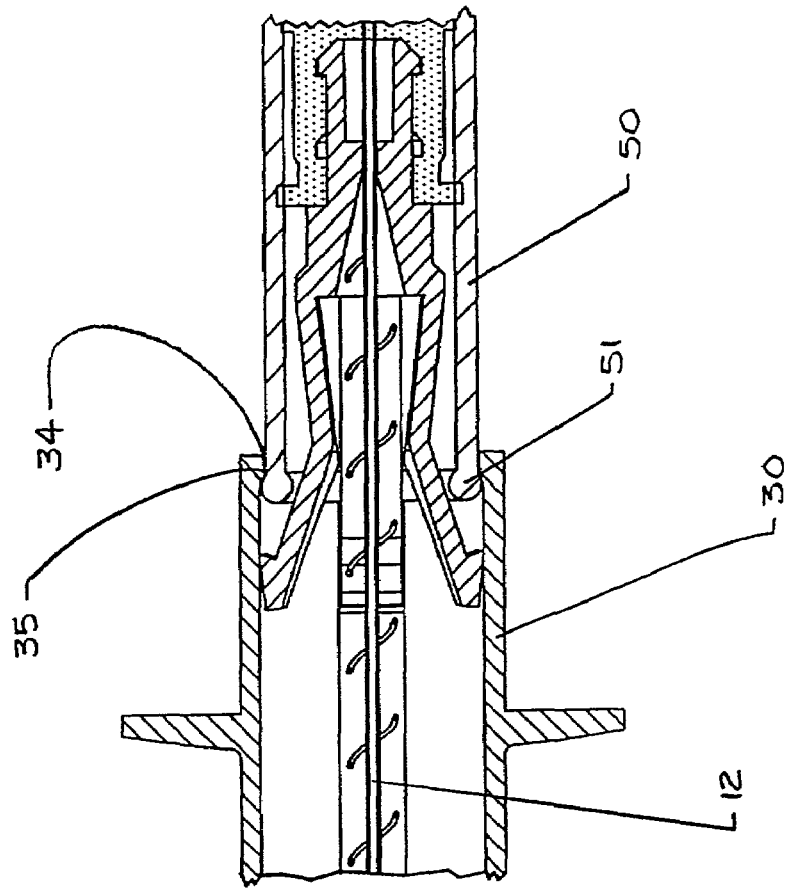
FIG. 11 is an enlarged fragmentary sectional view of the cartridge injector shown in FIG. 1, illustrating the tamper resistant connection between the cartridge and barrel after the needle is retracted.

Preferably, the injection device 10 includes a mechanism to limit tampering or removal of the cartridge 50 from the barrel socket 34. Referring now to FIG. 11, the present embodiment includes an annular lip 35 that projects radially inwardly from the inside wall of the socket 34 in barrel 30. The lip 35 is adapted to seat against the beaded rim 51 on the cartridge 50 so that the cartridge can not be easily pulled out of the rear of the barrel 30. As a result, access to the retracted elements, and the contaminated needle in particular, is limited.

Referring now to FIGS. 4–10, the operation of the injection device 10 will be described. Prior to use, the needle 12 is disposed in an extended position so that the distal end 16 of the needle projects forwardly from the barrel 30, as shown in FIG. 4. Preferably, the device 10 is shipped with the cartridge 50 already mounted in barrel 30 so that the barbed connector 25 is engaged in the first recess 82a. Alternatively, the cartridge 50 may be shipped separately from the barrel 30, so that the cartridge must be attached to the barrel prior to use.

With the cartridge 50 and barrel 30 assembled, the device 10 is held vertically so that the distal end 16 of needle 12 points upwardly. The user holds the device 10 by placing the user's thumb in a supporting position beneath the thumb pad 42 of plunger 40. In addition, the user places a finger over each finger grip 36 to control the operation of the device 10. With the user's fingers anchored over the finger grips 36, the user applies a slight squeezing pressure on the thumb pad 42, much like a conventional syringe. The squeezing pressure displaces the cartridge 50 forwardly relative to the barrel so that the barbed connector 25 on the needle retainer 20 engages the second recess 82b in front seal 80 and the needle 12 pierces the wall 86. As the front seal 80 is pierced, entrapped air in the forward chamber 56 is vented through needle 12.

Continued advancement of the plunger 40 drives the seal 70 toward the piercing element 64 until the piercing element pieces the mid seal, thereby providing fluid communication between the forward and rearward chambers 52, 56. At this point, the first component 54 may be advanced into the forward chamber 56. Pressure is applied on the thumb pad 42 until the first component 54 is completely expelled from the rearward chamber 52 into the forward chamber 56 and the forward end of the plunger meets the rearward end of the mid seal 70. The user then shakes the injector device 10 to mix the first and second components 54, 58 inside the forward chamber 56.

During mixing, the locking clip 100 prevents the cartridge 50 from being advanced forwardly into the needle retainer 20. This constraint on the cartridge 50 limits the potential for inadvertent discharge of the medication 59 from the needle 12 and premature needle retraction. Once the medication 59 is adequately mixed, the user removes the locking clip 100 from the barrel 30 so that the cartridge 50 can be advanced forwardly within the barrel. At this point, initial pressure applied to the thumb pad 42 advances the cartridge and vents excess air out of the second chamber 56.

The needle is then inserted into a patient and the plunger 40 is depressed to axially advance the cartridge 50 relative to the barrel 30, thereby injecting the medication 59 from the cartridge into the patient. At the end of the injection stroke, the beaded rim 51 on the cartridge 50 engages the retaining arms 22, thereby displacing the retaining tabs 24 radially inwardly to disengage the needle retainer 20 into the unlocked position. Although the needle retainer 22 is in the unlocked position, the needle 12 does not retract until the user releases pressure from the thumb pad 42. In this way, the user can retain pressure on the thumb pad 42 until after the needle is withdrawn from the patient. The user can then release pressure from the thumb pad 42 so that the needle is propelled rearwardly by the spring 26. Alternatively, the user can release pressure from the thumb pad 42 while the needle 12 is still inserted in the patient. Once the thumb pad 42 is released, the spring 26 propels the needle 12 rearwardly so that the contaminated distal tip 16 of the needle is enclosed within the barrel 30.

Figure 12:
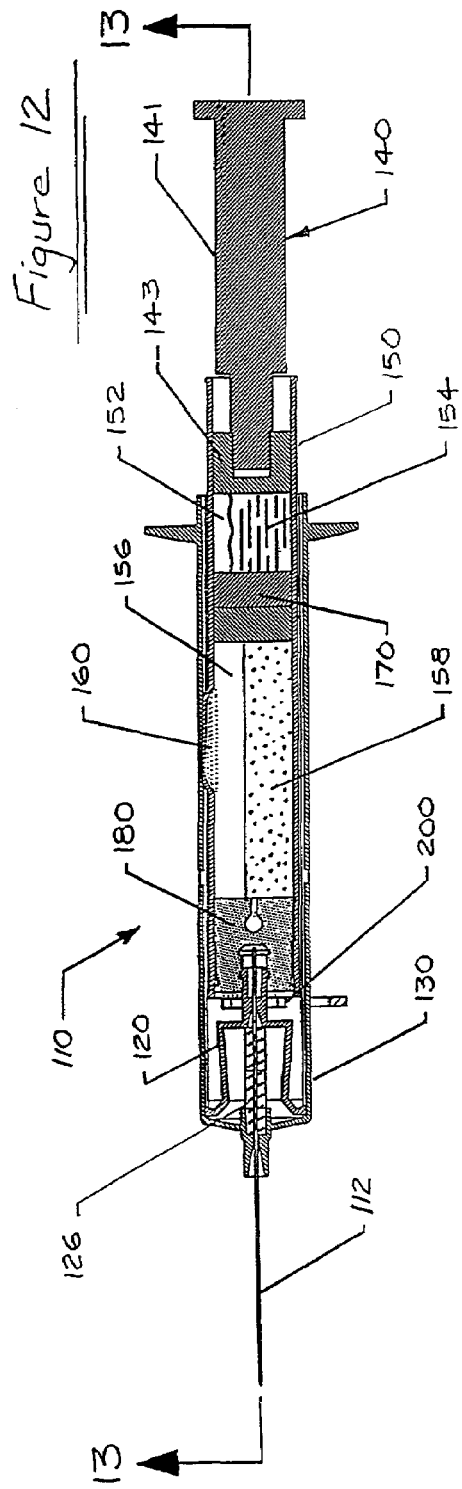
FIG. 12 is a sectional view of a second embodiment of a two-chambered pre-filled cartridge injector having a retractable needle.
Figure 13:
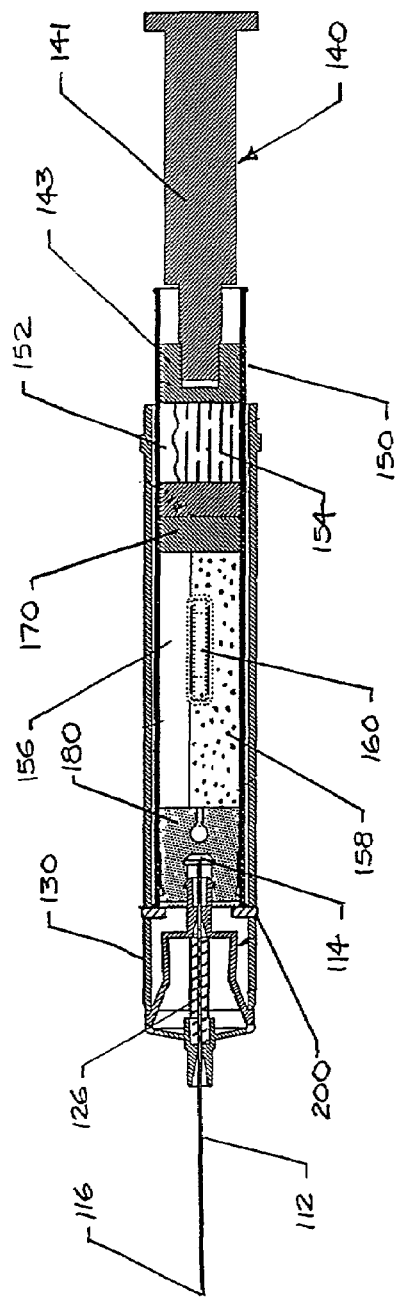
FIG. 13 is a sectional view of the device shown in FIG. 12 taken along the line 13—13.

Referring now to FIGS. 12–16 in general, and to FIGS. 12–13 specifically, a second embodiment of a pre-filled safety diluent injector is shown. The injector device 110 includes elements that are substantially similar to the elements described above in connection with the first embodiment 10, illustrated in FIGS. 1–11. These elements include: a double-ended needle 112, a generally cylindrical barrel 130, a compression spring 126, a needle retainer 120 releasably retaining the needle against the bias of the spring, a locking clip 200. The needle 112 has a sharpened proximal tip 114 and a sharpened distal tip 116. The spring 126 circumscribes the needle 112 and is compressed against the interior of the barrel 130 at the barrel's forward end. The rearward end of the spring 126 bears against the interior of the needle retainer 120 to bias the needle 112 and needle retainer in the rearward direction.

In contrast to the previous embodiment, the second embodiment utilizes a cartridge 150 having a selectively sealable by-pass fluid passage 160 to separate the two medicinal components, rather than a mid wall and a pierceable seal as described above with the first embodiment. Prior to use, a mid seal 170 within the cartridge 150 separates the two medicinal components 154, 158. Prior to use, the mid seal 170 is displaced forwardly adjacent the by-pass passage 160, which provides a fluid passage, allowing the two medicinal components 154, 158 to be mixed. The mixed components can then be injected into the patient.

Referring to FIGS. 12, 13, the detail of the Cartridge 150 will be described in greater detail. The cartridge is a generally cylindrical container. The forward end of the cartridge is sealed by the pierceable forward seal 180. The rearward end of the cartridge is sealed by a piston 143 that forms a fluid-tight seal with the interior wall of the cartridge. Intermediate the forward seal 180 and the piston 143, a mid seal 170 forms a fluid-tight seal with the interior wall of the cartridge, separating the cartridge into two chambers, a forward chamber 156 for receiving a first component 158, and a rearward chamber 152 for receiving a second component 154.

The cartridge 150 includes a bubble-like fluid passage 160 that protrudes outwardly from the side of the cartridge. The fluid passage 160 forms an area in which the diameter of the cartridge is greater than the diameter of the mid seal. The fluid passage 160 is an axially elongated channel having a length that is greater than the axial length of the mid seal 170, and preferably, is shorter than the combined length of the mid seal and the piston 143.

Although the fluid passage 160 is illustrated as a bubble-like protrusion, the fluid passage may be formed in other configurations. For instance, the fluid passage may be a recess or axial groove formed in the interior wall of the cartridge 150, so that the fluid passage does not protrude from the exterior surface of the cartridge. Similarly, the fluid passage may be an annular recess formed in the interior wall of the cartridge.

Referring to FIG. 12, the device 110 is illustrated in a "storage" position. In this position, the mid seal 170 prevents the two medicinal components from mixing. Therefore, the sealed cartridge 150 can be stored for an extended period, if desired, without compromising the efficacy of the medicinal components. In the stored position, the mid seal 170 is disposed rearwardly of the fluid passage 160 so a fluid-tight seal is formed between the mid seal and the interior wall of the cartridge, around the entire circumference of the mid seal.

During storage of the injection device 110, the medication is divided into two separate components stored in the cartridge 150, as shown in FIGS. 12–13. Specifically, the first component 154 of the medicine is stored in the first chamber 152 and the second component 158 of the medicine is stored in the second chamber 156. As discussed further below, preferably, when the cartridge is being filled during manufacture, a quantity of air remains within the second chamber 156.

A plunger 140 is slidably disposed in the rearward end of the cartridge 150. The plunger 140 is comprised of a plastic molded plunger rod 141 and an elastomeric piston 143. The piston 143 forms a fluid-tight seal with the inner wall of the cartridge, and is slidably displaceable within the cartridge. The plunger rod 141 can be connected to the plunger seal 143 in a number of ways. In the present embodiment, the plunger rod 141 includes external screw threads that are configured to engage internal threads inside the plunger seal 143, whereby the plunger rod and seal can be screwed together.

Referring now to FIG. 14, the transfer of the first medicine component 154 into the second chamber 156 shall be described. The mid seal 170 is advanced axially until it registers with the fluid passage 160. The fluid passage 160 then provides a by-pass passage so that the component in the rearward chamber can be injected into the forward chamber. Since the forward chamber preferably includes a quantity of air (or other compressible fluid), the material in the forward chamber can be compressed to allow the mid seal to be advanced into registry with the fluid passage 160. Alternatively, the forward chamber may include a vent for venting the air from the forward chamber when the fluid is transferred from the rearward chamber into the forward chamber. If a vent is included, preferably the vent is sealable to prevent leakage of the mixed components during injection.

Specifically, to mix the two components in the cartridge, the plunger 140 is axially advanced into the cartridge 150, to compress the first component 154 against the rearward end of the mid seal 170 in the first chamber 152. As back pressure on the mid seal 170 overcomes the frictional resistance between the mid seal and the cartridge 150, the mid seal is displaced forwardly in the cartridge. Once the mid seal 170 is displaced into alignment with the fluid passage 160, a passage is created between the mid seal and the inside wall of the fluid passage, as shown in FIG. 14.

The fluid passage 160 is sufficiently large to allow the first substance 154 to flow around the mid seal and into the second chamber 156 where it is mixed with the second substance 158. Once the first component is completely transferred to the second chamber 156, the plunger seal 143 is advanced until it abuts the mid seal 170, as shown in FIG. 15. The combined axial length of the mid seal 170 and piston 143 is slightly longer than the length of the fluid passage 160. Therefore, the mid seal and piston seal off the entire length of the fluid passage. This prevents the contents of the second chamber 156 from backflowing during mixing of the components.

Figure 16:
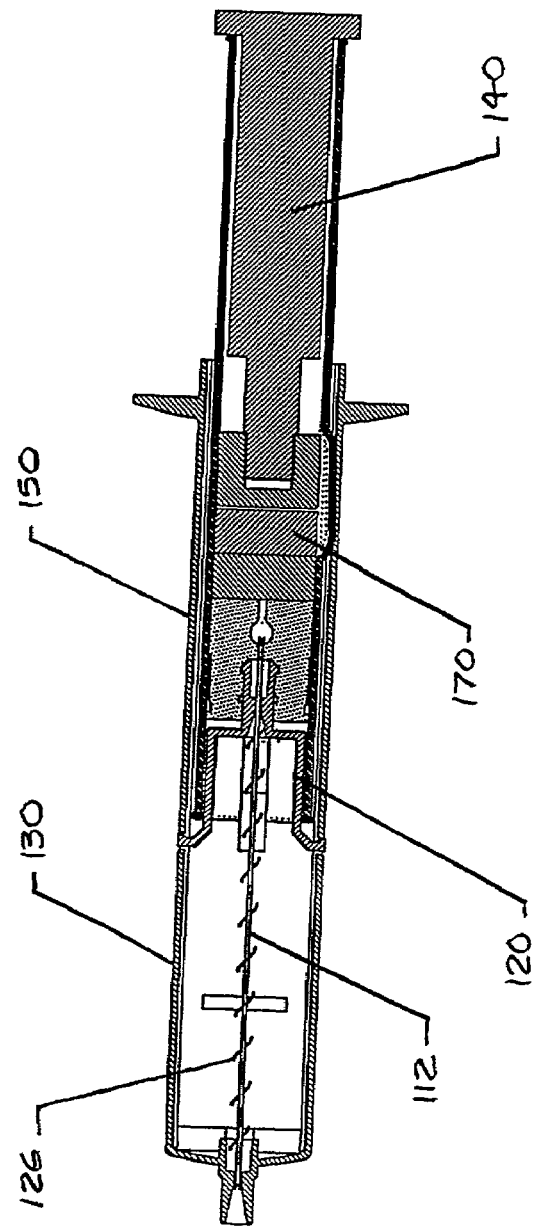
FIG. 16 is a sectional view of the device shown in FIG. 12 illustrating the device after needle retraction.

After mixing of the components is completed, the locking clip 200 is removed to allow injection of the medication into the patient. Pressure is applied to the cartridge 150 to discharge the medication from the second chamber 156. At the completion of the injection stroke, the cartridge 150 actuates the needle retainer 120. Pressure on the cartridge 150 is then released so that the needle can be retracted, as shown in FIG. 16.

Figure 17:
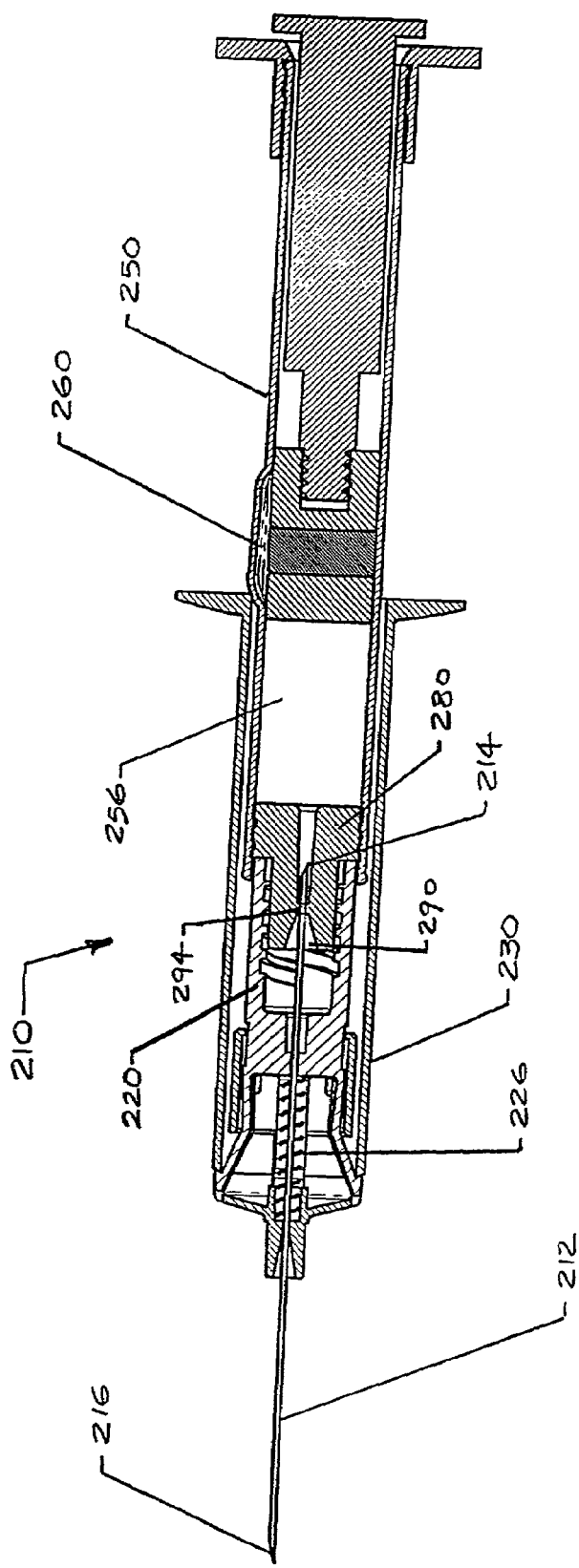
FIG. 17 is a sectional view of a third embodiment of a two-chambered pre-filled cartridge injector having a retractable needle.

Referring now to FIGS. 17–23 in general, and to FIG. 17 specifically, another embodiment of a pre-filled safety diluent injector is designated generally 210. The injector device 210 includes a double-ended needle 212, a generally cylindrical barrel 230 that houses the needle and a generally cylindrical cartridge 250. The barrel 230 further includes a compression spring 226 and a needle retainer 220 releasably retaining the needle 212 against the bias of the spring. The needle 212 has a sharpened rearward tip 214 and a sharpened forward tip 216. The spring 226 circumscribes the needle 212 and is compressed against the interior of the barrel 230 at the barrel's forward end. The rearward end of the spring 226 bears against the interior of the needle retainer 220 to bias the needle 212 and needle retainer in the rearward direction.

In this embodiment, the transferring and mixing of the medication components is done in the cartridge 250 prior to attaching the cartridge to the needle hub 221. Since the cartridge 250 is not connected to the needle assembly during mixing, there is no risk of inadvertently retracting the needle during the mixture of the components. As a result, the barrel does not include a locking clip, as in the other embodiments.

Referring now to FIGS. 18–19, the cartridge 250 and barrel 230 are packaged and distributed so that the two are disassembled. The cartridge 250 is a generally cylindrical vessel that may be molded out of pharmaceutical quality glass such as borosilicate or a rigid inert plastic such as polyolefin or polyester. A cartridge cap 253 is disposed over the distal end of the cartridge 250. The cartridge 250 is configured similar to the cartridge 150 illustrated in FIGS. 12–16, and includes a bubble-like fluid passage 260 that protrudes outwardly from the side of the cartridge. A mid seal 270 is slidably disposed in the cartridge 250 and divides the cartridge into a first chamber 252 and a second chamber 256. Each chamber of cartridge 250 is filled with a predetermined amount of a component of medication during manufacturing of the device 210. In particular, the first chamber 252 is prefilled with a first component 254 of the medication and the second chamber 256 is prefilled with a second component 258.

Referring now to FIG. 20, a plunger 240 is slidably disposed in the proximal end of the cartridge 250. The plunger 240 is comprised of a plastic molded plunger rod 241 and an elastomeric plunger seal 243. When the plunger 240 is axially advanced into the cartridge 250, the first component 254 is compressed against the rearward end of the mid seal 270 in the first chamber 252. As back pressure on the mid seal 270 overcomes the frictional resistance between the mid seal and the cartridge 250, the mid seal is displaced forwardly in the cartridge. Once the mid seal 270 is displaced into alignment with the fluid passage 260, a passage is created between the mid seal and the inside wall of the fluid passage to allow the first substance 254 to flow around the mid seal and into the second chamber 256 where it is mixed with the second substance 258.

The fluid passage 260 is sufficiently long to allow the first substance 254 to flow around the mid seal and into the second chamber 256 where it is mixed with the second substance 258. Once the first component is completely transferred to the second chamber 256, the plunger seal 243 is advanced until it abuts the mid seal 270, as shown in FIG. 21. The combined axial length of the mid seal 270 and plunger seal 243 is slightly longer than the maximum length of the fluid passage 260 so that the mid seal and plunger seal close off the entire length of the fluid passage. This prevents the contents of the second chamber 256 from backflowing during mixing of the components.

Referring again to FIG. 18, the cartridge 250 includes an elastomeric front seal 280 in the distal end of the cartridge. The front seal 280 may be molded of a self-sealing biocompatible elastomer such as polyisoprene. The front seal 280 is generally cylindrical with a wide cylindrical rearward end 282 disposed within the cartridge and a reduced diameter forward end 284 projecting forwardly from the forward end of the cartridge. The rearward end 282 has an outside diameter that is similar to the inside diameter of the cartridge 250. In addition, the rearward end 282 has a plurality of axially-spaced circumferential ribs 286 that frictionally and sealingly engage the interior of the cartridge to provide a fluid tight seal and prevent fluid from leaking from the cartridge.

The forward end 284 of front seal 280 includes an external thread 288 about its circumference. The distal end 284 also contains a shallow frontal cavity 290. A narrow bore 292 in fluid connection with the second chamber 256 extends from the proximal end of the front seal 280 and terminates within the reduced diameter distal end 284. Fluid communication between the frontal cavity 290 and the bore 292 is obstructed by a pierceable membrane 294.

Referring now to FIG. 19, the barrel 230 is generally cylindrical and has a tapered nose 232 at its distal end. The nose 232 has an opening through which the needle 212 extends. In addition, the nose 232 is configured to receive a needle cover 211 that fits over the nose to prevent accidental needle sticks when the needle 212 is in an extended position. The proximal end of the barrel 230 is open, forming a cylindrical socket 234 adapted to receive the cartridge 250. Prior to attachment with the cartridge 250, the rearward open end of the barrel 230 is closed by a cylindrical barrel cap 233. The barrel further includes a pair of retaining apertures 238 that cooperate with the needle retainer 220 to releasably retain the needle, and a pair of lockout windows that cooperate with locking tabs to lock the needle in the retracted position.

The needle retainer 220 includes a generally cylindrical body 221 and a pair of retaining arms 222 that extend radially forwardly from the body 221. A generally cylindrical aperture 296 is disposed within the proximal end of the needle retainer body 221. The inner wall of the aperture 296 includes internal screw threads 298 that are adapted to receive the external screw thread 288 of the front seal 280 in the cartridge 250.

The cartridge cap 253 and barrel cap 233 are removed from the cartridge 250 and barrel 230, respectively, to prepare the cartridge and barrel for assembly. The cartridge 250 is connected to the barrel 230 by inserting the forward end of the front seal through the open end of the barrel 230 and screwing the cartridge clockwise into the aperture 296. The frontal cavity 290 in the front seal 280 is preferably coaxial with the needle 212, such that attachment of the cartridge 250 to the barrel 230 causes the proximal needle tip 214 to enter the cavity 290 and pierce the membrane 294, thereby connecting the second chamber of the cartridge in fluid communication with the needle 212, as shown in FIG. 17.

Referring to FIG. 17, the cartridge 250 is connected to the barrel 230, the medication can be injected into the patient by advancing the cartridge forwardly into the barrel. The proximal end of the front seal 280 is configured to form a sliding fit with the interior of the cartridge 250 so that the cartridge slides over the front seal during advancement of the cartridge. As the cartridge 250 is advanced, the rearward end of the front seal 280 bears against the needle retainer 220, thereby keeping the front seal stationary during advancement of the cartridge. At the same time, the mid seal 270 at the rear of the second chamber 256 is displaced toward the front seal 280. This causes a reduction of volume in the second chamber 256, whereby the medication is displaced into the needle to facilitate the injection. At the completion of the injection, the mid seal 270 bears against the rearward end of the front seal 280, as shown in FIG. 22.

As in the previous embodiments, the needle 212 is retracted by actuating the needle retainer 220. In particular, the needle 212 is retracted by disengaging the retaining arms 222 from the retaining apertures 238 in the barrel wall to allow the spring 226 to propel the needle 212 rearwardly. To actuate the needle retainer 220, pressure is applied to the cartridge 250 to advance the cartridge over the needle retainer body 221, as shown in FIG. 22. During advancement, the distal end of the cartridge 250 engages a cylindrical sleeve 300 that is disposed around the distal end of the needle retainer body 221. The inside and outside diameters of the release sleeve 300 are preferably equal to the inside and outside diameters of the cartridge 250 so that the distal end of the cartridge mates with the proximal end of the sleeve. Prior to engagement with the cartridge 250, axial movement of the release sleeve 300 along the needle retainer is limited by an internal flange 302 that slides within an annular fluid passage 223 on the needle retainer body 221. After the cartridge 250 engages the sleeve 300 continued advancement of the cartridge drives the sleeve axially forwardly into engagement with the retaining arms 222. The release sleeve 300 deflects the retaining arms radially inwardly and out of engagement with the retaining apertures 238, allowing the spring 226 to propel the needle 212 rearwardly, as shown in FIG. 23.

As described above, the third embodiment includes a threaded engagement between the front seal 280 and the needle retainer 220 rather than a barbed connection as described in the first two embodiments. Using a threaded connection can increase the overall length of the needle retainer 220, which in turn increases the distance between the distal end of the cartridge 250 and the retaining arms 222. One manner for accommodating this increased length is to increase the length of the barrel 230. However, by incorporating the release sleeve 300, the length of the barrel 230 need not be substantially increased. The release sleeve 300 compensates for the increased distance by acting as an extension of the cartridge 250. This eliminates the need to increase the overall length of the device 210. Preferably, the length of the release sleeve 300 is slightly longer than the length of the threaded engagement between the front seal 280 and the needle retainer 220.

Figure 24:
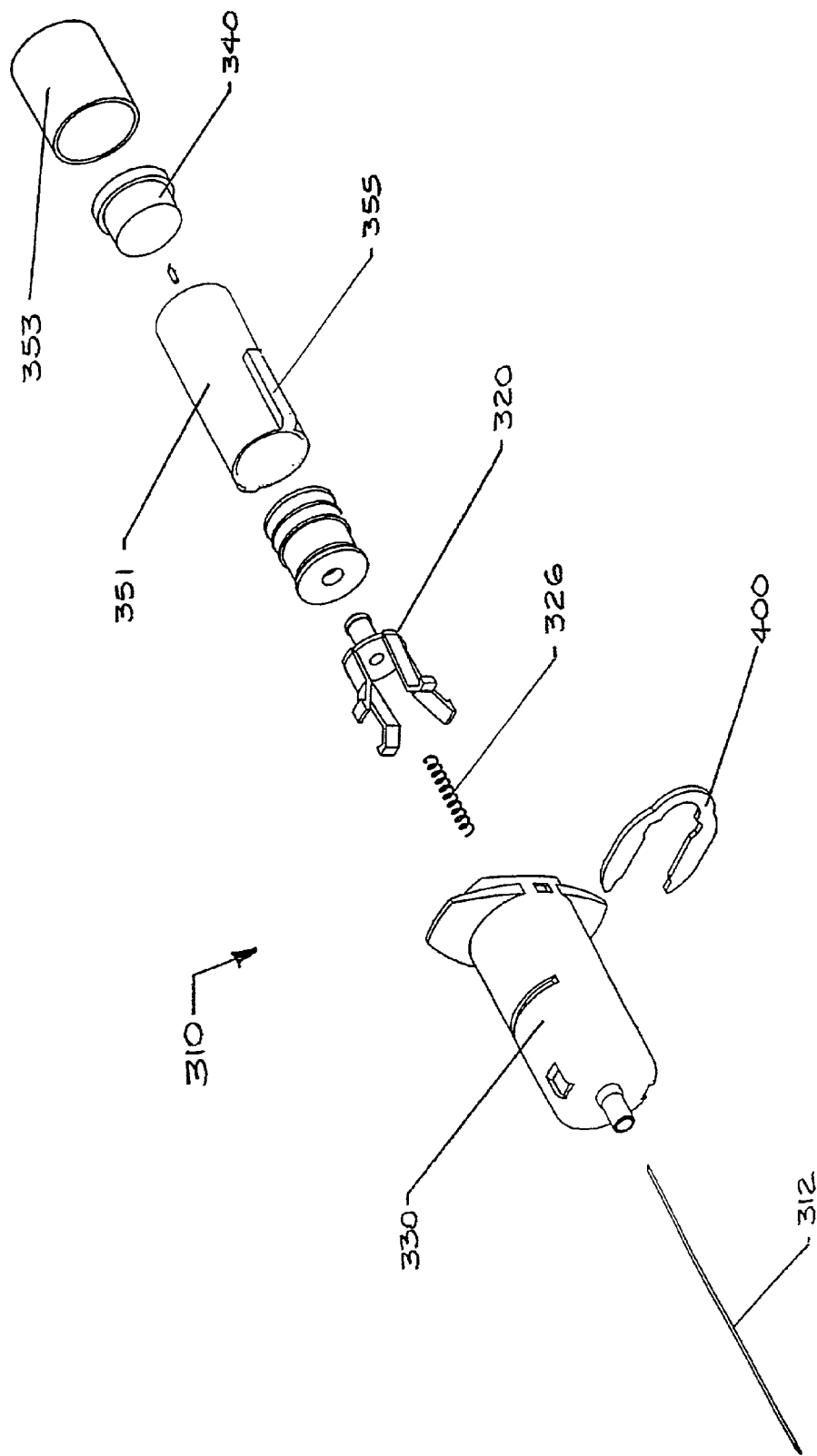
FIG. 24 is an exploded perspective view of a fourth embodiment of a two-chambered pre-filled cartridge injector having a retractable needle.
Figure 25:
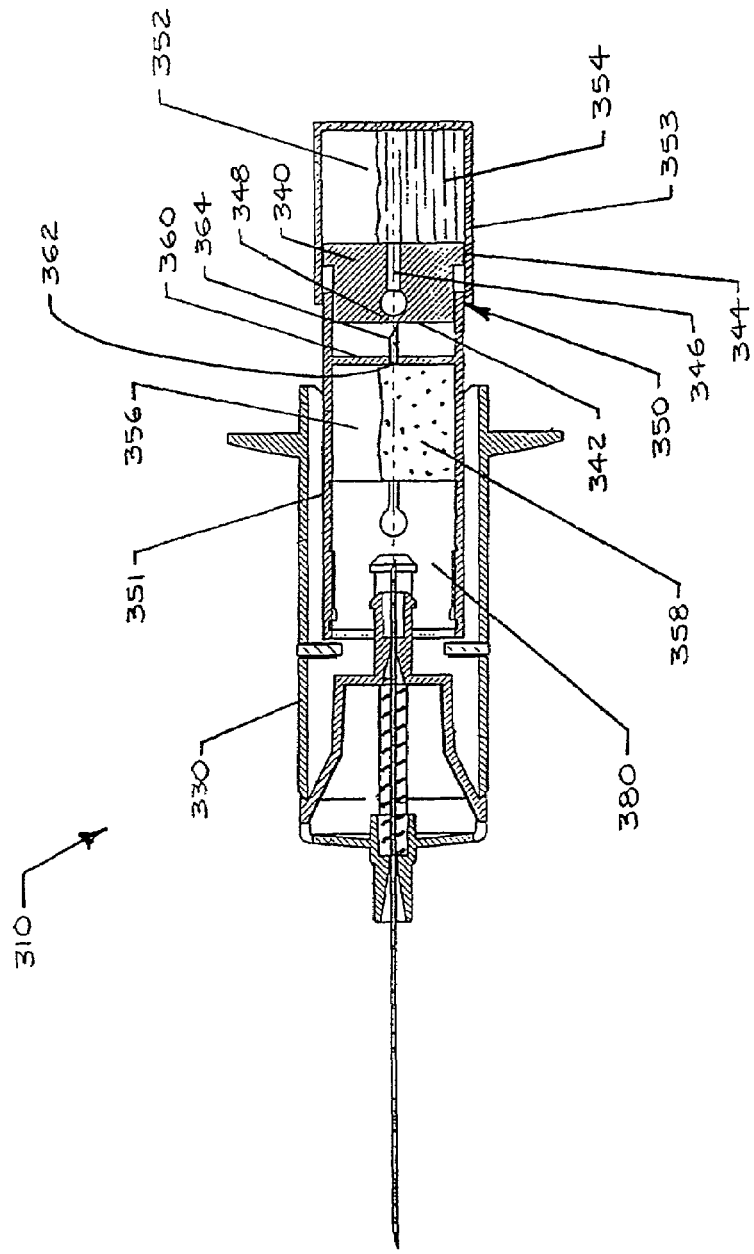
FIG. 25 is a sectional view of the device illustrated in FIG. 24.

Referring now to FIGS. 24–29 in general, and to FIGS. 24–25 specifically, a fourth embodiment of a pre-filled safety diluent injector is shown. The injector device 310 includes a double-ended needle 312, a generally cylindrical barrel 330 that houses the needle and a generally cylindrical cartridge assembly 350 mounted within the proximal end of the barrel. Like the previous embodiments, the barrel further includes a compression spring 326 and a needle retainer 320 releasably retaining the needle 312 against the bias of the spring. The device 310 also includes a U-shaped locking clip 400 in the barrel wall to prevent accidental discharge of medication from the device 310.

The cartridge assembly 350 has a two-part design that offers the advantage of using cost-efficient plastic in the assembly. The cartridge assembly 350 includes a front cylinder 351 having an open proximal end and a rear cylinder 353 having an open distal end telescopically mounted to the proximal end of the front cylinder. The front cylinder 351 contains an internal wall 360 that divides the cartridge assembly 350 into a first chamber 352 and a second chamber 356. The first chamber 352 contains a predetermined amount of a first component 354 of medication, and the second chamber 356 contains a predetermined amount of a second component 358 of medication. The proximal end of the front cylinder 351 is closed by a pierceable elastomeric front seal 380.

In many applications, the second component 358 will be a dry powdered component. Dry components do not require a glass container and can be stored in plastic containers without jeopardizing long term stability of the component. Since it is more cost-efficient to mold complex parts out of plastic than glass, it is preferable to minimize the complexity of the glass portion of the cartridge assembly 350. To this end, the front and rear cylinders 351, 353 are configured so that the first component 354 is stored entirely within the rear cylinder and the second component 356 is stored entirely within the front cylinder. In this arrangement, the front cylinder 351 comprises a more complicated structure to allow the rear cylinder to be a simple cup-shaped container. Therefore, the more complex forward cylinder can be molded out of cost-efficient plastic for those devices that store a dry second component 358 in the second chamber 356. Preferably, glass is only used, if at all, to mold the rear cylinder 353.

As stated earlier, the rear cylinder 353 is telescopically mounted on the proximal end of the front cylinder 351. The outside diameter of the rear portion of the rear seal is generally equal to the inside diameter of the rear cylinder 353 so as to frictionally engage the interior of the rear cylinder and provide a fluid tight seal. The rear cylinder 353 is adapted to slide axially over the rear seal 340 in response to pressure applied to the proximal end of the rear cylinder.

The barrel 330 has an inside diameter large enough to accommodate the outside diameter of the rear cylinder 353. As a result, the outside wall of the front cylinder 351 is separated from the interior wall of barrel 330 by a clearance space, as shown in FIG. 25. The front cylinder 351 is maintained in a concentric relationship with the much larger barrel 330 by a pair of opposing longitudinal ribs 355 on the outside wall of the front cylinder. The longitudinal ribs are illustrated in FIG. 24.

An elastomeric rear seal 340 is disposed between the front cylinder 351 and rear cylinder 353. The rear seal 340 includes a reduced diameter end 342 partially disposed in the open proximal end of the front cylinder 351. The rear seal 340 also includes a flanged end 344 disposed within the rear cylinder 353. The reduced diameter end 342 and flanged end 344 frictionally and sealingly engage the interior of the front cylinder 352 and rear cylinder 354, respectively. This engagement provides a fluid tight seal with the interior of both cylinders, while allowing the rear seal 340 to be displaced relative to either cylinder. Forward advancement of the rear seal 340 relative to the front cylinder 351 is limited by the proximal end of the front cylinder, which is configured to matingly engage the flanged portion of the rear seal.

As stated earlier, the front cylinder 351 contains an internal wall 360. The internal wall 360 is adjacent the rearward open end of the cartridge, forming a socket for receiving the rear seal 340. The internal wall 360 contains an orifice 362 mounted in the center of the wall 360. A hollow piercing member 364 is mounted in the orifice and extends rearwardly toward the rear seal 340. In addition, it may be desirable to provide a vent opening in the internal wall 360 to vent the air between the rear seal 340 and the internal wall when the rear cylinder is advanced to pierce the rear seal.

The distal end of the rear seal 340 is closed by a membrane 348 that is configured to be pierced by piercing member 364. The rear seal 340 includes a hollowed mid section 346 that is connected in fluid communication with the first chamber 352 through the proximal end of the rear seal. Once the membrane 348 is pierced, a fluid passage is created through the piercing member 364 and rear seal 340, such that the first and second chambers, 352, 356 are connected in fluid communication. The rear seal 340 may be molded in a high elongation self-sealing biocompatible elastomer, such as polyisoprene.

The operation of the device 310 will now be described. A slight squeezing pressure is applied to the proximal end of the rear cylinder 353 to axially advance the rear cylinder over the front cylinder 351. This causes the first component 354 to become compressed between the rear seal 340 and the closed proximal end of the rear cylinder 353. Continued pressure on the rear cylinder 353 creates back pressure on the rear seal 340 which axially displaces the rear seal forwardly into the piercing member 364. At this time, the membrane 348 is pierced to create a fluid passage between the first and second chambers 352, 356.

Figure 26:
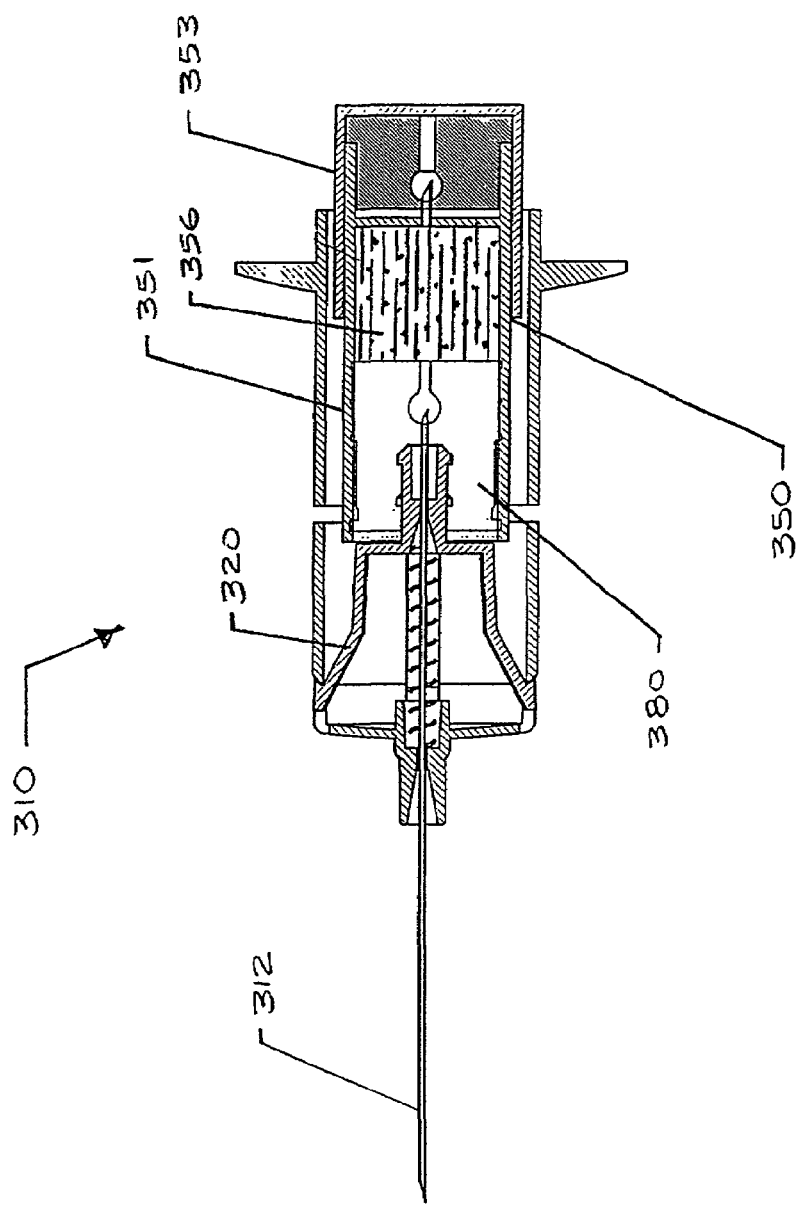
FIG. 26 is a sectional view of the device in FIG. 24 illustrating the device after mixture of the medical components.

The rear cylinder 353 is advanced forwardly relative to the front cylinder 351 to expel the first component 354 from the first chamber 352 into the second chamber 356. Once the first component 354 is completely expelled from the first chamber 352, additional pressure on the rear cylinder 353 advances the rear cylinder forwardly relative to the front cylinder 351 until the closed proximal end of the rear cylinder abuts the proximal end of the rear seal 340, as shown in FIG. 26. At this point, the device 310 is shaken to mix the components within the second chamber 356. During the mixing process, displacement of the cartridge assembly 350 is prevented by the locking clip 400, thereby minimizing the potential for accidental discharge of the medication.

Figure 27:
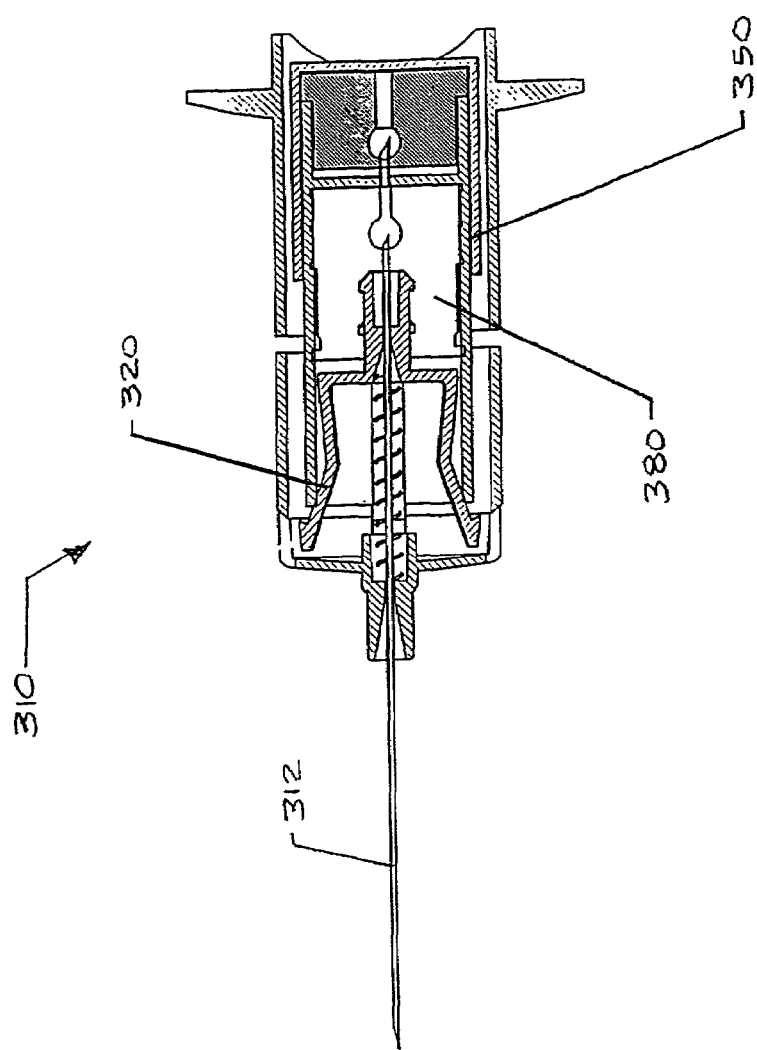
FIG. 27 is a sectional view of the device shown in FIG. 24 illustrating the device at the completion of an injection.

After the components are mixed, the locking clip 400 is removed. The cartridge assembly is then displaced forwardly so that the rearward end of the needle 312 pierces the forward seal 380. The air is then vented from the forward chamber. Further pressure is applied to the cartridge assembly 350 to discharge the medication from the second chamber 356 and through the needle 312. At the completion of the injection stroke, the proximal end of the cartridge assembly 350 actuates the needle retainer 320, as shown in FIG. 27. Pressure on the cartridge assembly 350 is then released so that the needle 312 can be retracted, as shown in FIGS. 28 and 29.

In some instances, it may be desirable to store the cartridge in its component parts. In other words, the rear cylinder 353 may be detached from the forward cylinder 351. Prior to use, the rear cylinder 353 would be attached to the forward cylinder 351 and the combined assembly would be utilized as described above. In such instances, the separate rear container 353 may include a separate cap to cover its forward end. Similarly, the forward cylinder 351 may include a cap to cover its rearward end. The detachable rearward cylinder 353 may permit a variety of pre-measured medicinal components to be stored and readily combined in various combinations prior to use.

The terms and expressions which have been employed are used as terms of description and not of limitation. There is no intention in use of such terms and expressions of excluding any equivalents of the features shown and described or portions thereof. It is recognized, however, that various modifications of the embodiments described herein are possible within the scope and spirit of the invention. For instance, the embodiments described above include a needle retainer having a pair of radially displaceable arms to automatically release the needle for retraction after use. However, the devices may be modified by utilizing different needle retainers that may or may not automatically retract the needle after use. Accordingly, the invention incorporates variations that fall within the scope of the following claims.

What is claimed is:

1. A medical device, comprising:
   a barrel having an open proximal end and a distal end;
   a needle having a first sharpened tip and being operable between an extended position in which the first sharpened tip projects forwardly from the barrel and a shielded position in which the first sharpened tip is shielded to prevent inadvertent contact with the first sharpened tip;
   a cartridge in fluid communication with the needle, comprising:
      a first chamber containing a first substance;
      a second chamber containing a second substance;
      a fluid flow controller between the first chamber and the second chamber; and
   a plunger slidably disposed within the cartridge;
   a biasing element imparting a force capable of displacing the needle relative to the barrel to shield the first sharpened tip; and a needle retainer releasably retaining the needle in the extended position;

wherein axially advancing the plunger within the first chamber advances the first substance through the fluid flow controller and into the second chamber where said first substance combines with the second substance to form a medicinal mixture, and continued advancement of the plunger and cartridge relative to the barrel after the mixture is expelled from the cartridge actuates the needle retainer to release the needle, whereupon the biasing element displaces the needle relative to the barrel to shield the first sharpened tip.

2. The medical device in claim 1 wherein the medical device further comprises a needle carrier fixed to the needle.

3. The medical device in claim 1 wherein the needle has a second sharpened tip at its rearward end.

4. The medical device in claim 1 wherein the needle is retracted upon release of pressure on the plunger.

5. The medical device in claim 1 wherein the medical device further comprises one or more stops that impede continued rearward displacement of the first sharpened needle tip beyond the proximal end of the barrel as the needle is moved to the shielded position.

6. The medical device in claim 1 wherein the plunger is comprised of a plastic molded plunger rod connected to an elastomeric seal.

7. The medical device in claim 1 wherein the plunger is displaceable relative to the cartridge while the first substance is expelled from the first chamber, and the plunger is stationary relative to the cartridge when the mixture is expelled from the second chamber.

8. The medical device in claim 1 wherein the second substance is a powdered material.

9. The medical device in claim 1 wherein the second substance is a liquid material.

10. The medical device in claim 1 wherein the volume of the second chamber is greater than the combined volume of the first substance and the second substance.

11. The medical device in claim 1 wherein the fluid flow controller comprises:
a wall between the first and second chambers having an opening;
a hollow piercing element disposed through the opening having a sharpened end extending into the first chamber; and
a fluid flow pathway through the piercing element;
wherein axially displacing the cartridge toward the barrel displaces the
plunger until the plunger is ruptured by the piercing element, creating a passage through the plunger which aligns with the fluid flow pathway in the piercing element to allow the first substance to pass through the plunger into the second chamber.

12. The medical device in claim 1 wherein the fluid flow controller comprises:
a barrier between the first and second chambers having an opening;
a hollow piercing element disposed through the opening having a sharpened end extending into the first chamber;
a fluid flow pathway through the piercing element; and
a pierceable mid seal axially displaceable within the first chamber that provides fluid communication between the first and second chambers upon being pierced by the piercing element;
wherein axially displacing the plunger toward the barrel displaces the pierceable mid seal until the mid seal is ruptured by the piercing element, creating a passage through the mid seal which aligns with the fluid flow pathway in the piercing element to allow the first substance to pass through the mid seal into the second chamber.

13. The medical device in claim 1 wherein the fluid flow controller comprises:
a mid seal between the first and second chambers that is axially displaceable within the cartridge; and
an elongated fluid passage in the side wall of the cartridge;
wherein axially displacing the plunger toward the barrel displaces the mid seal into alignment with the fluid passage, creating a passage between said mid seal and the inside wall of the fluid passage that allows the first substance to flow around the mid seal into the second chamber.

14. The medical device in claim 1 wherein the cartridge is substantially permanently attached to the barrel.

15. The medical device in claim 1 wherein the cartridge comprises a beaded circumferential rim on the distal end of the cartridge, and the barrel contains a lip projecting radially inwardly from the inner bore of the barrel at the barrel's proximal end, said lip adapted to engage the beaded rim of the cartridge to impede removal of the cartridge from the rear of the barrel after needle retraction.

16. The medical device in claim 2 wherein the biasing element comprises a compression spring disposed between the distal end of the barrel and the needle carrier.

17. The medical device in claim 2 wherein the needle retainer comprises a pair of forward tines extending radially outwardly from the needle carrier and configured to releasably engage a pair of windows in the barrel wall.

18. The medical device in claim 2 wherein a cylindrical sleeve having generally the same outside diameter as the cartridge is disposed around the circumference of the needle carrier in general axial alignment with the cartridge, such that axial advancement of the cartridge at the end of the injection stroke displaces the sleeve toward the distal end of the barrel to actuate the needle retainer.

19. The medical device in claim 3 wherein the cartridge further comprises a front seal at the distal end of the cartridge that is configured to be pierced by the second sharpened tip to connect the needle and second chamber in fluid communication.

20. The medical device in claim 19 wherein the minimum axial force on the plunger that is required to pierce the front seal is less than or equal to the minimum axial force required to axially displace the plunger in the rear chamber.

21. The medical device in claim 19 wherein the distal end of the front seal includes an external thread and the proximal end of the needle carrier includes a cavity adapted to receive the threaded end of the front seal.

22. A medical device, comprising:
a barrel having an open proximal end, a distal end and an opening through the barrel wall oriented perpendicularly to the longitudinal axis of the barrel;
a needle having a first sharpened tip and being operable between an extended position in which the first sharpened tip projects forwardly from the barrel and a shielded position in which the first sharpened tip is shielded to prevent inadvertent contact with the first sharpened tip;
a cartridge in fluid communication with the needle, comprising:
a first chamber containing a first substance;
a second chamber containing a second substance;

a fluid flow controller connecting the first chamber and the second chamber; and a plunger slidably disposed within the cartridge;

a biasing element imparting a force capable of displacing the needle relative to the barrel to shield the first sharpened tip;

a needle retainer releasably retaining the needle in the extended position; and a locking clip detachably connected to the barrel;

wherein axially advancing the plunger within the first chamber advances the first substance through the fluid flow controller and into the second chamber where said first substance combines with the second substance to form a medicinal mixture, and removal of the locking clip from the barrel permits further advancement of the plunger and cartridge relative to the barrel to expel the mixture from the second chamber, whereafter axially advancing the cartridge disengages the needle retainer to allow the biasing element to displace the needle relative to the barrel to shield the first sharpened tip.

23. The medical device in claim 22 wherein the medical device further comprises a needle carrier fixed to the needle.

24. The medical device in claim 22 wherein the needle has a second sharpened tip at its rearward end.

25. The medical device in claim 22 wherein the needle is retracted upon release of pressure on the plunger.

26. The medical device in claim 22 wherein the cartridge comprises a beaded circumferential rim on the distal end of the cartridge, and the barrel contains a lip projecting radially inwardly from the inner bore of the barrel at the barrel's proximal end, said lip adapted to engage the beaded rim of the cartridge to impede removal of the cartridge from the rear of the barrel after needle retraction.

27. The medical device in claim 22 wherein the medical device further comprises one or more stops that impede continued rearward displacement of the first sharpened tip beyond the open proximal end of the barrel as the needle is moved to the shielded position.

28. The medical device in claim 22 wherein the plunger is comprised of a plastic molded plunger rod connected to an elastomeric seal.

29. The medical device in claim 22 wherein the plunger is displaceable relative to the cartridge while the first substance is expelled from the first chamber, and the plunger is stationary relative to the cartridge when the mixture is expelled from the second chamber.

30. The medical device in claim 22 wherein the locking clip comprises a flat U-shaped disk having a plurality of teeth along the inner edge, said clip being configured to slide through the slits in the barrel in a direction perpendicular to the longitudinal axis of the barrel and at a location between the cartridge and the needle retainer, thereby impeding contact between the cartridge and the needle retainer.

31. The medical device in claim 22 wherein the second substance is a powdered material.

32. The medical device in claim 22 wherein the second substance is a liquid material.

33. The medical device in claim 22 wherein the volume of the second chamber is greater than the combined volume of the first substance and the second substance.

34. The medical device in claim 22 wherein the fluid flow controller comprises:

a barrier between the first and second chambers having an opening;

a hollow piercing element disposed through the opening having a sharpened end extending within the first chamber;

a fluid flow pathway through the piercing element; and a pierceable mid seal axially displaceable within the first chamber that provides fluid communication between the first and second chambers upon being pierced by the piercing element;

wherein initial axial displacement of the plunger toward the barrel displaces the pierceable mid seal into contact with the piercing element, piercing the mid seal and creating a passage through the mid seal which aligns with the fluid flow pathway in the piercing element to allow the first substance to pass through the mid seal into the second chamber.

35. The medical device in claim 22 wherein the fluid flow controller comprises:

a mid seal between the first and second chambers that is axially displaceable within the cartridge; and an elongated fluid passage in the side wall of the cartridge between the mid seal and the distal end of the cartridge;

wherein axially displacing the plunger toward the barrel displaces the mid seal into alignment with the fluid passage, creating a passage between said mid seal and the inside wall of the fluid passage that allows the first substance to flow around the mid seal into the second chamber.

36. The medical device in claim 23 wherein the biasing element comprises a compression spring disposed between the distal end of the barrel and the needle carrier.

37. The medical device in claim 23 wherein the needle retainer comprises a pair of forward windows in the barrel wall and a pair of forward tines extending radially outwardly from the needle carrier and configured to releasably engage the forward windows.

38. The medical device in claim 24 wherein the cartridge further comprises a front seal at the distal end of the cartridge that is configured to be pierced by the second sharpened tip to connect the needle and second chamber in fluid communication.

39. The medical device in claim 38 wherein the minimum axial force on the plunger that is required to pierce the front seal is less than or equal to the minimum axial force required to axially displace the plunger in the rear chamber.

40. A medical device, comprising:

a barrel having an open proximal end and a distal end;

a needle having a first sharpened tip and being operable between an extended position in which the first sharpened tip projects forwardly from the barrel and a shielded position in which the first sharpened tip is shielded to prevent inadvertent contact with the first sharpened tip;

a cartridge in fluid communication with the needle, comprising:

a first chamber containing a first substance;

a second chamber containing a second substance;

a fluid flow controller between the first chamber and the second chamber; and a biasing element imparting a force capable of displacing the needle relative to the barrel to shield the first sharpened tip; and a needle retainer releasably retaining the needle in the extended position;

wherein the fluid flow controller is adapted to keep the first and second substances separate prior to use, and also adapted to allow mixing of the first and second substances prior to an injection, wherein after use the needle is disposed in the shielded position.

* * * * *